(12) United States Patent
Starr et al.

(10) Patent No.: US 10,667,754 B2
(45) Date of Patent: Jun. 2, 2020

(54) DEVICES AND METHODS FOR PARAMETER MEASUREMENT

(71) Applicant: THE BOARD OF REGENTS OF THE UNIVERSITY OF TEXAS SYSTEM, Austin, TX (US)

(72) Inventors: Peter Starr, San Antonio, TX (US); Steven Bailey, San Antonio, TX (US); Mauli Agrawal, San Antonio, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 16/163,661

(22) Filed: Oct. 18, 2018

(65) Prior Publication Data
US 2019/0282173 A1    Sep. 19, 2019

Related U.S. Application Data

(63) Continuation of application No. 15/102,900, filed as application No. PCT/US2014/069525 on Dec. 10, 2014, now abandoned.
(Continued)

(51) Int. Cl.
*G01L 9/00* (2006.01)
*A61B 5/00* (2006.01)
(Continued)

(52) U.S. Cl.
CPC .......... *A61B 5/6862* (2013.01); *A61B 5/0004* (2013.01); *A61B 5/0031* (2013.01); *A61B 5/0084* (2013.01); *A61B 5/0215* (2013.01); *A61B 5/02158* (2013.01); *A61B 5/1036* (2013.01); *A61B 5/1038* (2013.01); *A61B 5/1473* (2013.01); *A61B 7/023* (2013.01); *A61F 2/24* (2013.01); *A61M 1/106* (2013.01); *A61M 1/1037* (2013.01); *A61M 1/1053* (2013.01); *B29C 65/48* (2013.01); *G01L 9/0072* (2013.01); *A61B 5/03* (2013.01); *A61B 5/145* (2013.01); *A61B 2017/00345* (2013.01);
(Continued)

(58) Field of Classification Search
CPC ....... G01L 9/00; G01L 9/0041; G01L 9/0042; G01L 9/0072; G01L 13/025
See application file for complete search history.

(56) References Cited

U.S. PATENT DOCUMENTS 3,640,271 A    2/1972   Horton
4,838,088 A    6/1989   Murakami
(Continued)

FOREIGN PATENT DOCUMENTS

EP          0904009          9/2003
WO    WO 1995/020769        8/1995
(Continued)

OTHER PUBLICATIONS

An Introduction to MEMS (Micro-Electromechanical Systems); Prime Faraday Partnership, 2002.
(Continued)

*Primary Examiner* — Natalie Huls
(74) *Attorney, Agent, or Firm* — Parker Highlander PLLC

(57) ABSTRACT

A thin-film, diaphragm based device is disclosed which can be used to perform an array of sensing and actuating operations where a very thin profile is desired, such as in millimeter, micrometer, or nanometer tight spaces.

17 Claims, 32 Drawing Sheets

Related U.S. Application Data

(60) Provisional application No. 61/914,473, filed on Dec. 11, 2013.

(51) Int. Cl.

| | |
|---|---|
| *A61B 5/0215* | (2006.01) |
| *A61B 5/103* | (2006.01) |
| *A61M 1/10* | (2006.01) |
| *A61B 5/1473* | (2006.01) |
| *A61B 7/02* | (2006.01) |
| *A61F 2/24* | (2006.01) |
| *B29C 65/48* | (2006.01) |
| *A61B 5/145* | (2006.01) |
| *A61B 17/00* | (2006.01) |
| *A61M 1/12* | (2006.01) |
| *A61B 5/03* | (2006.01) |
| *B29L 31/00* | (2006.01) |

(52) U.S. Cl.
CPC . *A61B 2562/0204* (2013.01); *A61B 2562/028* (2013.01); *A61B 2562/0233* (2013.01); *A61B 2562/0247* (2013.01); *A61B 2562/0285* (2013.01); *A61B 2562/04* (2013.01); *A61B 2562/12* (2013.01); *A61B 2562/164* (2013.01); *A61M 1/101* (2013.01); *A61M 1/1086* (2013.01); *A61M 1/12* (2013.01); *A61M 1/122* (2014.02); *A61M 1/125* (2014.02); *B29L 2031/753* (2013.01); *B81B 2201/0264* (2013.01)

(56) References Cited

U.S. PATENT DOCUMENTS

| | | |
|---|---|---|
| 5,471,723 A | 12/1995 | Luder et al. |
| 5,619,997 A | 4/1997 | Kaplan |
| 5,719,740 A | 2/1998 | Hayashi et al. |
| 6,152,181 A | 11/2000 | Wapner et al. |
| 6,312,380 B1 | 11/2001 | Hoek et al. |
| 6,352,874 B1 | 3/2002 | McNeil et al. |
| 6,426,582 B1 | 7/2002 | Niederer et al. |
| 6,431,005 B1 | 8/2002 | Delaye |
| 6,458,618 B1 | 10/2002 | Allen et al. |
| 6,461,301 B2 | 10/2002 | Smith |
| 6,504,795 B1 | 1/2003 | Niederer et al. |
| 6,770,032 B2 | 8/2004 | Kaplan |
| 6,795,374 B2 | 9/2004 | Barnes et al. |
| 6,855,115 B2 | 2/2005 | Fonseca et al. |
| 6,907,787 B2 | 6/2005 | Cook et al. |
| 6,959,608 B2 | 11/2005 | Bly et al. |
| 7,000,298 B2 | 2/2006 | Cook et al. |
| 7,073,397 B2 | 7/2006 | Ganapathi et al. |
| 7,082,835 B2 | 8/2006 | Cook et al. |
| 7,165,455 B2 | 1/2007 | Magee et al. |
| 7,205,701 B2 | 4/2007 | Liu et al. |
| 7,353,719 B2 | 4/2008 | Hiura et al. |
| 7,452,334 B2 | 11/2008 | Gianchandani et al. |
| 7,549,962 B2 | 6/2009 | Dreschel et al. |
| 8,162,839 B2 | 4/2012 | Kaplan |
| 8,393,223 B2 | 3/2013 | Delapierre et al. |
| 8,760,031 B2 | 6/2014 | Chang |
| 2004/0211260 A1 | 10/2004 | Girmonsky et al. |
| 2006/0287602 A1 | 12/2006 | O'Brien et al. |
| 2007/0186667 A1 | 8/2007 | Deangelis et al. |
| 2008/0281210 A1 | 11/2008 | Nunez et al. |
| 2011/0007178 A1 | 1/2011 | Kahlman |
| 2011/0265574 A1 | 11/2011 | Yang |
| 2012/0019013 A1 | 5/2012 | Everett et al. |
| 2013/0137958 A1 | 5/2013 | Tai et al. |

FOREIGN PATENT DOCUMENTS

| | | |
|---|---|---|
| WO | WO 2001/012092 | 2/2001 |
| WO | WO 2010/081134 | 7/2010 |

OTHER PUBLICATIONS

Andle and Vetelino, "Acoustic wave biosensors," *Sensors and Actuators A: Physical*, 44(3):167-176, 1994.

Arya et al, "Prevalence of peripheral arterial disease in a cohort of diabetic patients," *South Med J.*, 99(6):564-9, 2006.

Borner et al., "Ultrasonic measurements with micromembranes," Sensors and Actuators A 46-47, 62-65, 1995.

Boulton et al., "Comprehensive foot examination and risk assessment: a report of the task force of the foot care interest group of the American Diabetes Association, with endorsement by the American Association of Clinical Endocrinologists. AU. American Diabetes Association, American Association of Clinical Endocrinologists," *SO Diabetes Care*, 31(8):1679, 2008.

Cavanagh et al., "Ulceration, unsteadiness, and uncertainty: The biomechanical consequences of diabetes mellitus," *Journal of Biomechanics*, 26(1):23-29, 31-40, 1993.

CDC National Diabetes Facts Sheet, 2011: http://www.cdc.gov/diabetes/pubs/estimates11.htm, 2011.

Chevrier et al., "An infrared pneumatic detector made by micromachining technology," *Journal of Micromechanics and Microengineering*, 5(2):193, 1995.

Chow, "Fully Wireless Implantable Cardiovascular Pressure Monitor Integrated with a Medical Stent," *IEEE Transactions on Biomedical Engineering*, 57(6), 2010.

Collins, "Miniature Passive Pressure Transensor for Implanting in the Eye," *IEEE Transactions on Biomedical Engineering*, BME-14(2):74-83, 1967.

Driver et al., "The costs of diabetic foot: the economic case for the limb salvage team," *Journal of Vascular Surgery*, 52(3):17S-22S, 2010.

Engel et al., "Development of polyimide flexible tactile sensor skin," *Journal of Micromechanics and Micoengineering*, 13(3):359, 2003.

Hirose, "Information technology on five senses," *Advance Industrial Science and Technology*, 2005.

Huff, "A pressure-balanced electrostatically-actuated microvalve," *IEEE*, pp. 1123-127, 1990.

Huff, "Flow Characteristics of a Pressure-Balanced Microvalve," 7th International Conference on Solid-State Sensors and Actuators. Yokohama, Japan, Proceedings of Transducers: 98-101, 1993.

Lin et al., "Free swelling and confined smart hydrogels for applications in chemomechanical sensors for physiological monitoring," *Sensors and Actuators B: Chemical*, 136(1): 186-195, 2009.

Mannsfeld et al., "Highly sensitive flexible pressure sensors with micro-structured rubber dielectric layers," *Nat. Mater.*, 9(10): 859-864, 2010.

Margolis et al., "Prevalence of diabetes, diabetic foot ulcer, and lower extremity amputation among Medicare beneficiaries, 2006 to 2008: Data Points #1," In: Data Points Publication Series [Internet]. Rockville (MD): Agency for Healthcare Research and Quality (US). Available from: http://www.ncbi.nlm.nih.gov/books/NBK63602/, Feb. 17, 2011.

Murphy, "Continuous In Vivo Blood Pressure Measurements Using a Fully Implantable Wireless SAW Sensor," *Biomed Microdevices*, 15:737-749, 2013.

Office Communication issued in U.S. Appl. No. 15/102,900, dated Oct. 5, 2017.

PCT International Search Report and Written Opinion issued in International Application No. PCT/US2014/069525, dated Mar. 24, 2015.

Schroth et al., "A Resonant Polyimide-based Humidity Sensor," The 8th International Conference on Solid-State Sensors and Actuators and Eurosensors IX, pp. 740-742, 1995.

Singh et al., "Preventing Foot Ulcers in Patients with Diabetes," *JAMA*, 293(2), 2005.

Sivaramakrishnan et al., "Electrically stretched capacitive membranes for stiffness sensing and analyte concentration measurement," *Sensors and Actuators B: Chemical*, 135(1): 262-267, 2008.

Takahata et al., "A Wireless Microsensor for Monitoring Flow and Pressure in a Blood Vessel Utilizing a Dual-Inductor Antenna Stent and Two Pressure Sensors," 17th IEEE International Conference on Micro Electro Mechanical Systems (MEMS), pp. 216-219, 2004.

(56) References Cited

OTHER PUBLICATIONS

Takahata et al., "Stentenna: a micromachined antenna stent for wireless monitoring of implantable microsensors," In: Engineering in Medicine and Biology Society, Proceedings of the 25th Annual International Conference of the IEEE, pp. 3360-3363, 2003.

Young et al., "Less Invasive Long-Term Implantable Blood Pressure Sensing System for Small Animal Real-Time Monitoring," retrieved from the Internet at https://www.researchgate.net/publication/228554255_Less-Invasive_Long-Term_Implantable_Blood_Pressure_Sensing_System_for_Small_Animal_Real-Time_Monitoring, retrieved Jun. 21, 2017.

Zengerle et al., "A bidirectional silicon micropump," Micro Electro Mechanical Systems, EMS '95, Proceedings. *IEEE,* pp. 19-24, 1995.

--- Embedded Coil

| | Acoustic Impedance Z (MRayls) |
|---|---|
| Stainless Steel | ~45 |
| Silicon / Glass / Quartz | ~12 |
| Soft Tissue | ~1.65 |
| Air | 0.0004 |

| | Reflected Pressure Ratio (Reflected / Incident) | Reflected Power Ratio (Reflected / Incident) |
|---|---|---|
| Soft Tissue – Glass | 76% | 58% |
| Soft Tissue – SS | 93% | 86% |
| Soft Tissue – Air | >99% | >99% |

DEVICES AND METHODS FOR PARAMETER MEASUREMENT

This application is a continuation of U.S. patent application Ser. No. 15/102,900, filed Jun. 9, 2016, which is a national phase application under 35 U.S.C. § 371 of International Application No. PCT/US2014/069525, filed Dec. 10, 2014, which claims the benefit of U.S. Provisional Patent Application No. 61/914,473, filed Dec. 11, 2013, the entirety of each is incorporated herein by reference.

BACKGROUND INFORMATION

Most MEMS sensors are built onto silicon based wafers of approximately 500 μm thickness. While these thick substrates confer stability during fabrication and over the long term, the thickness limits applications in tight spaces, which includes many biomedical and industrial conditions. The rigidity and biocompatibility of silicon based sensors are additional limiting factors. Overcoming these issues is particularly challenging for diaphragm based sensors, due to the tight control required to build three-dimensional cavities and diaphragms at such a small scale.

The active region of many silicon based sensors is the deflecting diaphragm near the surface of the sensor. Typically, the active region ranges from the low-micron to sub-micron scale, which is a small fraction of the overall sensor thickness. The sensor profile can be significantly reduced if the inactive substrate is replaced with a thinner substrate or if the active region is integrated into the device package.

Passive ultrasonic sensors, methods and systems for their use are described in U.S. Pat. No. 6,770,032. Specifically, passive acoustic sensors having at least two flat parallel acoustically reflecting surfaces. At least one reflecting surface is on a member which is movable such that the distance between the reflecting surfaces varies as a function of a physical variable to be determined. Preferably, the sensor is made such that the intensity of a first portion of incident acoustic waves which is reflected from one reflecting surface is equal or substantially similar to the intensity of a second portion of the incident acoustic waves which is reflected from the other reflecting surface. The first portion and the second portion interfere to form a returning acoustic signal having one or more maximally attenuated frequencies which is correlated with the value of the physical variable. The internal acoustic signal is received and processed to determine the value of the physical variable from one or more of the maximal attenuation frequencies. Methods and systems for using the passive sensors are disclosed.

Existing systems such as those described above use an ultrasound probe, with a limited transmitting/receiving bandwidth, which permitted limited sensing of resonators, because most feasible mechanical resonators have natural frequencies in the audible or just above audible range under physiologically relevant pressure.

A passive sensor system using ultrasonic energy is also described in PCT Patent Publication WO 1995020769. In particular, a passive sensor system (14) utilizing ultrasonic energy is disclosed. The passive sensor system includes at least one ultrasonically vibratable sensor (10) and an ultrasonic activation and detection system (20, 22, 24, 25). The sensor (10) has at least one vibration frequency which is a function of a physical variable to be sensed. The ultrasonic activation and detection system (20, 22, 24, 25) excites the sensor and detects the vibration frequency from which it determines a value of the physical variable. The sensor includes (see FIG. 2-4) a housing, a membrane which is attached to the housing and which is responsive to the physical variable, a vibratable beam attached to the housing at one end and a coupler, attached to the membrane and to a small portion of the vibratable beam, which bends the vibratable beam in response to movement of the membrane.

The ability to measure pressure locally can be used in the analysis of certain conditions. Diabetics are prone to foot ulceration, with a population prevalence of approximately 8% and a lifetime risk of up to 25% (Margolis, Boulton). Loss of innervation due to diabetic peripheral neuropathy induces muscle laxity and associated skeleton deformities, as well as loss of sensation. This increased risk of focal stress points and reduced ability to accommodate to the initiating trauma greatly contribute to the formation of ulcers, which can progress in severity to the point where amputation is necessary. Critically, prevention and management by proper monitoring of foot conditions could reduce amputations by 50% (Driver).

Treatment of an ulcer is difficult after formation due to repetitive damage and compromised healing in diabetics. Over a third of the direct expenditure on diabetes in the US ($116 billion) is on ulcer treatment, with each treatment costing on average $28,000. Prevention by careful monitoring of the condition of the feet is considered to be the best approach and is thought to potentially avert half of the amputations due to ulceration (Driver).

Space constrictions limit conventional sensing devices in many environments, such as in shoes or insoles. Wires, power supplies, circuitry, and antennas in conventional approaches are all too large and cumbersome to fit without disruption. Electromagnetic resonance sensing offers a solution because these simple wireless systems only require a coil and a capacitor to operate. As such, they can be made small enough to wirelessly sense otherwise inaccessible environments. They are interrogated wirelessly by magnetic coupling. In some cases, the resonant system can entirely replace the conventional radio link system; in other cases, it can be used together with a radio link to extend the sensing range. The mechanism of resonance sensing is not widely used or known, probably because most sensing environments are accessible via wired sensors. Presently, to synthesize this mechanism of sensing with an application in foot pressure sensing requires a breadth of knowledge in a numerous disparate fields, including physics, mechanics, electrical engineering, and clinical medicine.

Peripheral neuropathy contributes to the high prevalence of foot ulceration in diabetics. Several systems, integrated into shoe insoles and socks, are currently available for monitoring foot pressures to prevent ulceration. However, these systems have practical limitations and inconveniences for end user, such as dangling wires or tenuous electronics.

Embodiments of the present disclosure offer a clean solution through a resonant wireless system in a shoe insole. The sensing insole is physically simple and durable, requires no on-site power supply or circuitry, and can wirelessly transmit pressure signals to a nearby device with radio link capability, such as a clip on the outer shoe, an anklet, or a waist belt. To our knowledge, no resonant wireless sensing system has been applied to measuring foot pressures in the patent or scientific literatures. An embodiment has been enabled with a thin film capacitive pressure transducer which demonstrates functionality and excellent pressure sensitivity.

SUMMARY

Described herein is a thin-film, diaphragm based device which can be used to perform an array of sensing and actuating operations anywhere where a very thin profile is desired, such as in millimeter, micrometer, or nanometer tight spaces. The device has a diaphragm and can operate by capacitive, resistive, and resonant mechanisms. Due to its general structure, applications include: mechanical sensing and actuation, chemical-biological sensing, and optical sensing.

The device can be bonded to any substrate, allowing for device integration. Additionally, the device can be constructed from flexible materials, which allows for applications which require flexibility, conformation to a nonflat or mobile surface, or in three dimensional configurations. The device can also be fabricated as an array of diaphragms to measure single factors, to measure multiple factors simultaneously, or to measure surface maps of factors. The fields of application are wide ranging, from biomedical to industrial. The thin film sensor can be considered a platform technology for low profile MEMS sensing due to its general structure and utility.

The dimensions and materials of commercially available pressure transducers limit their applications for intravascular and implantable blood pressure sensing. Here, a high fidelity pressure transducer is presented which is ~10 um thick and can be embedded into any surface, including cardiovascular catheters, guide-wires, and stents. The transducer is microfabricated from various polyimides, and is bonded onto 50 um thick 316L stainless steel foil for prototyping.

The static and dynamic characteristics of the transducer are excellent. The transducer signal has high linearity (R2>0.99), and resolution <<1 mmHg which is limited only by the system noise. The operating frequency range is from 0 to >1 kHz, which is well over the necessary limit for dynamic cardiovascular applications, even in small animals with rapid heart rates. Additionally, theoretical analysis indicates that both static and dynamic performance of the transducer can be further improved with optimization. Stability studies of the transducer in a pulsatile flow environment with saline and serum show little drift in transducer characteristics over a four week period.

Exemplary embodiments of the present disclosure relate to a thin-film sensing or actuating device. In certain embodiments, the device can be configured as a general sensor with broad ranging applications, as described in more detail below.

Exemplary embodiments include a thin film sensor which can be integrated onto any substrate, using methods that are compatible with a range of materials and sensing mechanisms. One embodiment is about 15 um, which has been bonded to a 50 um thick stainless steel substrate.

Exemplary embodiments include a device comprising: a substrate; and a diaphragm coupled to the substrate, wherein the diaphragm is a thin film capacitive transducer less than 1 mm thick. In particular embodiments, the thin film capacitive transducer is between 10 μm and 20 μm thick. In certain embodiments, the diaphragm is coupled to the substrate via an adhesive or other bonding method. Particular embodiments further comprise a chamber structure between the diaphragm and the substrate.

In specific embodiments, the diaphragm is coupled to the substrate via an adhesive; the chamber structure comprises a bonding pad around the perimeter of the chamber structure; and the chamber structure is positioned between the diaphragm and the adhesive layer. In certain embodiments, the substrate is electrically conductive. In particular embodiments, the substrate and diaphragm are configured as a wireless resonant pressure sensor sized for implantation in a human artery. In some embodiments, the diaphragm is approximately 15 μm thick, and in particular embodiments, the substrate is approximately 50 μm thick. In particular embodiments, the substrate is configured as an antenna. In specific embodiments, the device is configured to measure pressure with a linear sensitivity of approximately four percent between 0 and 400 mm Hg.

In certain embodiments, the substrate and the diaphragm are biocompatible. In particular embodiments, the device is configured as a pressure sensor. In some embodiments, the device is configured as an audio wave sensor. In specific embodiments, the device is configured as a chemical sensor. In some embodiments, the device is configured as a biological sensor. In certain embodiments, the device is configured as an optical sensor. In particular embodiments, the device is configured as a pump. In some embodiments, the device is configured as a valve. Particular embodiments further comprise a first electrode coupled to the diaphragm and a second electrode coupled to the substrate.

Exemplary embodiments also include a method of fabricating a thin film capacitive transducer, the method comprising; providing a substrate; providing a diaphragm, wherein the diaphragm is between 10 μm and 20 μm thick; and coupling the diaphragm to the substrate. In certain embodiments, coupling the diaphragm to the substrate comprises using adhesive to couple the diaphragm to the substrate. In particular embodiments, the method further comprises inserting a chamber structure between the diaphragm and the substrate before coupling the diaphragm to the substrate. In specific embodiments, the diaphragm and chamber structure are constructed using photolithography.

Described is a thin-film, diaphragm based device which can be used to perform an array of sensing and actuating operations anywhere where a very thin profile is desired, such as in millimeter, micrometer, or nanometer tight spaces. The device has a diaphragm and can operate by capacitive, resistive, and resonant mechanisms. Due to its general structure, applications include: mechanical sensing and actuation, chemical-biological sensing, and optical sensing.

The device can be bonded to any substrate, allowing for device integration. Additionally, the device can be constructed from flexible materials, which allows for applications which require flexibility, conformation to a nonflat or mobile surface, or in three dimensional configurations. The device can also be fabricated as an array of diaphragms to measure single factors, to measure multiple factors simultaneously, or to measure surface maps of factors. The fields of application are wide ranging, from biomedical to industrial. The thin film sensor can be considered a platform technology for low profile MEMS sensing due to its general structure and utility.

A mechanical resonator and system for acoustic wireless interrogation of the resonator are also disclosed. In certain embodiments, the resonator is micron-scale, with a resonance frequency that is strongly dependent on external pressure. Methods for interrogation of an implanted resonator include a skin piezo device which sends an impulse to the resonator. Induced resonance returns to the piezo a pressure wave at the pressure dependent frequency of the resonator. High resonance frequencies, >1 kHz, permit hundreds of pressure samples per second, which enables a dense recreation of the blood pressure waveform. Additional factors can be measured by the sensor, including temperature, local gas—fluid environment, and local viscosity.

In one embodiment, for example, it can be used in an implantable blood pressure sensing device where an ultra thin profile is important to successful implementation.

Cardiovascular problems can be addressed by one embodiment of the sensor, wherein a wireless implantable pressure sensor addresses the ubiquitous need for blood pressure monitoring and control, given the many conditions which hypertension negatively affects. Rates of heart attack, stroke, heart failure, and cardiac arrhythmias are all significantly increased at higher blood pressure levels. Exemplary embodiments of the device could serve as a monitoring of blood pressure for patients with a chronic cardiovascular condition to ensure compliance with treatment and as a warning system for an acute event. The potential demand is large as, according to the AHA, cardiovascular disease accounts for nearly $500 billion in cost, $75 billion of which is exclusive to hypertension and sequelae.

In certain embodiments, the device may comprise a sensing diaphragm that is approximately 15 µm thick, which is bonded to a stent material (e.g., 50 µm stainless steel). Exemplary embodiments can provide a linear sensitivity of about 4% over 400 mmHg. Exemplary embodiments provide good dynamic fidelity, and have been shown to accurately measure frequencies up to 10 kHz (and possibly higher, as higher frequencies have not been tested). In vitro studies are currently underway to characterize the robustness of the sensor over time. In vitro studies with the sensor and antenna in wireless mode are also planned in the future.

The device may be used in many applications, including for example: arrays of force/pressure sensors could be used as a tactile sensor, for diabetic patients with nerve damage and foot/skin ulcers, or for robotics applications. In addition, two pressure sensors spaced in a tube/artery can measure fluid flow rates by the pressure drop. In certain embodiments, the device can be used for mechanical sensing and actuation; bio-chemical sensing; optical sensing; implantable intravascular pressure monitoring; and cardio-vascular implants; and applications in implants for hearing loss.

In a specific embodiment, the device may be configured as a pressure sensor in an inductor-capacitor (LC) resonator for a wireless implantable blood pressure sensor. Such a device relates to a wireless implantable blood pressure sensor that reduces the thickness of the transducing element for its implementation in medium to small arteries, including the peripheral arteries. One aspect of the device replaces the thick silicon wafer onto which most pressure sensors are built with a very thin substrate or the surface of an existing device or implant. This substitution of platforms can save hundreds of micrometers of thickness. In addition, using the shape-memory NiTi as an antenna allows for an antenna that can be radially compressed and self-expand during a percutaneous catheter delivery of the device.

A wireless implantable pressure sensor that addresses the ubiquitous need for blood pressure monitoring and control and could serve as a monitoring of blood pressure (BP) for patients with a chronic cardiovascular condition to ensure compliance with treatment and as a warning system for an acute event. However, exemplary embodiments of the pressure transducer have applications beyond an implantable sensor.

With a diaphragm thickness of approximately 15 µm, the device could be bonded to the tip of a catheter for intravascular pressure sensing during operations. Biomedical applications beyond cardiovascular include ocular pressure sensing, compartment (syndrome) sensing, and integration into Lab-on-Chip (LOC) systems. Industrial applications include locations with heavy space constraints and/or need for physical flexibility, including robotics and tire pressure systems.

A thin film diaphragm sensor is described herein with multiple applications, including: mechanical sensing and actuation, chemical-biological sensing, and optical sensing. Exemplary embodiments of the device are approximately 10-20 µm thick and can be bonded to virtually any substrate. Exemplary embodiments may comprise a deflecting diaphragm mechanism which can be used under a variety of sensing and actuating mechanisms.

Certain exemplary embodiments of the device may be configured as a pressure sensor or an acoustic sensor. In the former, its thin profile can allow for implantable endovascular blood pressure monitoring. When coupled with a self-expanding coil composed of shape memory metal, it can be deployed conveniently through percutaneous catheterization and interrogated with a small coil near the skin surface. In an acoustic application, the device can provide for high transduction fidelity through the audible range.

Exemplary embodiments of the diaphragm device can be configured as closed cells or channels or as open cells or channels. The former configuration primarily serves in physical, mechanical, and resonance sensing and some forms of actuation. The latter configuration primarily serves in permittivity based sensing for biological and chemical factors, and some forms of actuation.

Closed cells are critical for establishing a pressure difference between the device chambers and the outside, which then allows for diaphragm deflection. Open cells are critical for allowing biological or chemical factors for permeating the inter-electrode space during permittivity based sensing. Additionally, access to the inter-electrode space is necessary in some forms of actuation, such as in pneumatic actuation of the diaphragm. Modes of Operation Exemplary embodiments of the disclosed diaphragm based device can be used in capacitive mode (two overlapping electrodes), in resistive mode (resistors on or within the diaphragm), in resonance mode (diaphragm is driven into mechanical resonance), or as a mechanical actuator. As described more fully below:

(1) Capacitive Mode $$Capacitance = \varepsilon A/z$$

$\varepsilon$—electrical permittivity of material/space between the electrodes

A—Area of overlapping electrodes z—gap between electrodes

Mechanisms of Capacitive Sensing

A factor that modifies any of these three properties can be sensed by a capacitive sensor.

(i) The most common sensing mechanism is by shifting the electrode gap ($\Delta z$) by diaphragm deflection. In this mode, force, pressure, and acoustic signals are typical measurands which are directly sensed. Numerous other factors can be indirectly sensed by a deflecting diaphragm. For instance, flow can also be measured with two pressure sensors in series. Additionally, biochemical factors and analytes can be sensed if a swelling smart material, for instance a receptor conjugated hydrogel, fills the electrode gap. Also, optical sensing can be achieved in a Golay cell configuration, described later.

(ii) Changing the permittivity ($\Delta \varepsilon$) is an additional sensing mechanism. Typically, a permeable material fills the space between electrodes and absorbs the factor or analyte. Absorption alters the permittivity and changes capacitance. Humidity and pH are commonly sensed by this mechanism, but an analyte specific material such as a receptor conjugated polymer (e.g., hydrogel) can allow for specific biochemical analytes to be sensed by this method. Additionally, a swelling hydrogel may combine the effects of permittivity shifts and diaphragm deflection.

(iii) Changing the area of overlapping electrodes (AA) is another sensing mechanism of capacitors with certain moving parts. Shear forces and acceleration by comb-drives or other arrangements are measured. However, since our capacitive sensor has fixed borders around the diaphragm, this mechanism does not apply.

(2) Resistive Mode

The most common pressure sensor is a deflecting diaphragm with a bridge of resistive sensors, either thin metal films or semiconductors. Deflection strains the diaphragm and its associated resistors, which then modifies their resistance.

In this mode, applications would likely be limited to force or pressure sensing, and their derivatives such as flow or acoustic sensing.

(3) Resonance Mode

The basic mechanism is that the diaphragm is driven into mechanical resonance and this resonance frequency is monitored. A factor which modifies this resonance frequency can then be detected.

A primary application of this sensing mechanism is for biological or chemical sensing. In this mode, the exposed surface of the diaphragm is conjugated with a receptor for the measured factor. Depending on its configuration, the diaphragm can be driven into resonance by various means, including electrostatically (if it contains parallel electrodes), thermally, or an applied pressure via an acoustic signal or a pop-test (a step drop in pressure, which induces resonance in the diaphragm). The resonance frequency can be monitored electrically by various methods which depend on whether the diaphragm device is acting as a variable capacitor or a variable resistor. When the biological or chemical factor binds the receptor, it mass loads the diaphragm and thereby shifts its resonance frequency.

(4) Mechanical Actuator

Whereas the sensing diaphragm moves in response to a signal, the diaphragm can alternatively be driven into movement to achieve a mechanical goal. Methods to induce mechanical actuation include pneumatic, electrostatic, thermal, among others. Most applications of a thin film mechanical actuator will likely lie in microfluidics devices, where the actuator can serve as a valve, a pump or other pressurizing device.

Sensing Types and Possible End Applications

Exemplary embodiments of the disclosed diaphragm based device can be used to achieve mechanical and physical sensing, mechanical actuation, biological and chemical sensing, and optical sensing, among others.

(1) Mechanical and Physical Sensing

The diaphragm device can operate as a force sensor under numerous configurations and conditions where a thin profile or flexibility is desired.

(i) Biomedical applications of force or pressure sensors include cardiovascular blood pressure or flow sensing (e.g., hypertension, heart failure), ocular pressure sensing (e.g., glaucoma), pulmonary pressure sensing (e.g., chronic obstructive pulmonary disease), pleural cavity pressure sensing (e.g., pneumothorax), urinary pressure sensing (e.g., incontinence), gastrointestinal pressure sensing (e.g., incontinence), peritoneal cavity pressure sensing (e.g., ascites), cerebro-spinal fluid pressure sensing (e.g., hydrocephalus), muscular pressure sensing (e.g., compartment syndrome), orthopedic pressure sensing (e.g., joint, disc, and/or implant pressures), podiatric pressure sensing (e.g., for diabetic ulcers) among others.

One particular use of high value would be on a catheter tip for intravascular blood pressure sensing or for urological sensing. Currently, in the hospital wards, fluid filled catheters transmit pressures from inside the body to an external pressure sensor. This arrangement has significant sensitivity and drift errors, in addition to artifacts such as the catheter whip effect, which reports artificially high spikes in pressure when the fluid filled catheter moves. Silicon microsensors do exist, but are very expensive (>$1k) and sterilization for re-use between patients is not common for safety reasons. An inexpensive, thin, flexible sensor which could be positioned at the tip of a disposable catheter could considerably improve pressure sensing accuracy. Additionally, a very thin profile would allow for measuring pressures in tighter spaces than are currently possible.

An additional application of high value for a thin pressure sensor is in implantable blood pressure sensing devices. Currently, silicon based microsensors are built onto silicon or silica chips which are at least several hundred microns in thickness. This thickness precludes applications in all but the largest arteries, since most medium and small arteries, such as the coronaries and peripheral arteries, are <4 mm in internal diameter. An implantable blood pressure sensing device has value in direct, continuous, and chronic monitoring of hypertension and heart failure, and can additionally serve as warning system for acute cardiovascular events. Such a device could be constructed as an inductor-capacitor (LC) system, with the thin pressure transducer in capacitive mode. It could also be constructed alternatively, where the transducer operates in either resistive or capacitive mode.

(ii) Capacitive microphones are very common for transducing audio signals. One biomedical application of a very thin audio transducer is in an unobtrusive hearing device, such as an inner ear implant, a cochlear implant, or hearing aid. The thinness is of particular relevance, as the tympanic membrane is ~50 um thick. Additionally, the sensing range is not necessarily limited to the audible range, however, and applications may include the sub-audible and ultrasound ranges.

(iii) Industrial applications for force and pressure sensing include automotive (e.g., tire pressure sensing, force sensors for monitoring shock, misalignment), machines and robotics (e.g., monitoring shock, misalignment), among others.

(iv) Robotics applications include artificial skin for tactile sensing. An array of diaphragms would allow for sensing a two dimensional surface map. Such an artificial skin could be used in a sensing skin for artificial intelligence robotics or in a prosthetic for sensory loss in humans.

(2) Mechanical Actuation

Most applications of a thin film mechanical actuator will likely lie in microfluidics devices, where the actuator can serve as a valve, a pump or other pressurizing device. As a valve, one or multiple diaphragms can situated as walls of a micro-channel. The diaphragm can be driven outward or inward for either by an electrostatic signal across the two electrodes or by a pneumatic signal from within the inter-electrode space. The valve state will be closed when the diaphragm is driven out and contacts the opposing wall, thereby occluding the channel. The valve state will be open when the diaphragm is driven in.

As a pump, the diaphragm can be driven to induce pressure to drive flow in an adjacent chamber or channel. Upstream the pump can be a one-way valve which blocks backwards flow, such that the pump only drives forward flow.

The diaphragm device could also operate as a miniature capacitive speaker, either in the sub-audible, audible, or ultrasound range. This mode of operation, the diaphragm would likely be driven electrostatically. As with the audio transducer operating in an unobtrusive hearing device, a miniature speaker could also be used in such a device for amplification of the audio signal.

(3) Biological and Chemical Sensing

Biological and chemical sensing in tight spaces has biomedical applications, among others in high technology. Possible transduction mechanisms include resonance or capacitive modes. An array of diaphragms could allow for monitoring of multiple markers.

This transducer could be used in an implantable device for monitoring biomarkers, for monitoring the status of either chronic disease or cancer. If configured to give surface map data, the device could be used as an artificial tasting or smelling device (smart tongue or smart nose).

(4) Optical Sensing

Indirect optical sensing can be achieved in a Golay cell configuration, whereby an air chamber with an optical filter sits atop the deflecting diaphragm. The optical signal enters the top chamber, changes its temperature, which induces expansion or contraction of the chamber volume, and thereby changes the applied pressure to the diaphragm of the capacitive sensor below.

If the sensor is configured as an array of frequency specific optical transducers, an optical camera can be achieved for imaging applications. A specific biomedical application of such an optical camera includes a retinal implant for restoring vision. The thin, flexible nature of the sensor confers a particular advantage for conforming to the curved topography of the eye.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "about", "approximately" or "substantially" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

DETAILED DESCRIPTION OF ILLUSTRATIVE EMBODIMENTS

Figure 1:
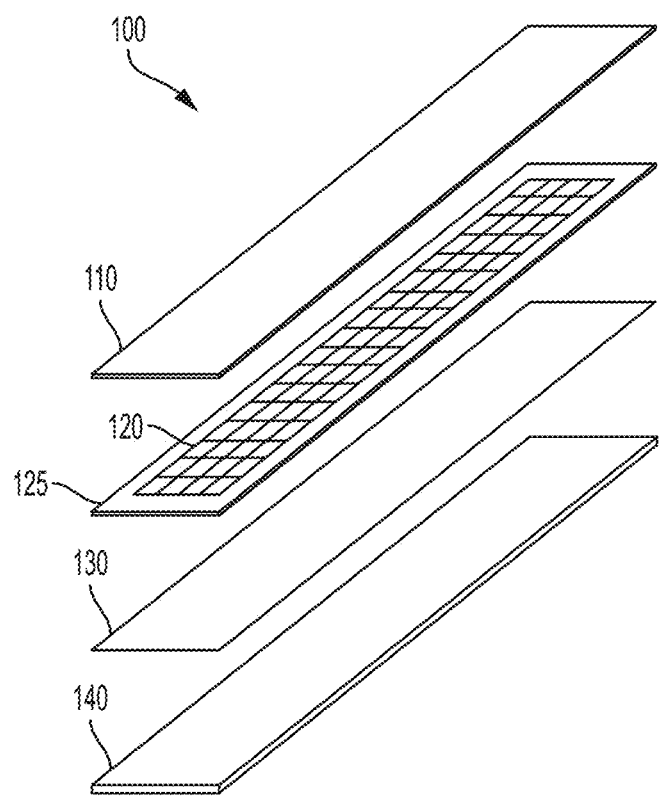
FIG. 1 shows an exploded view of one embodiment of a device according to the present disclosure.
Figure 2:
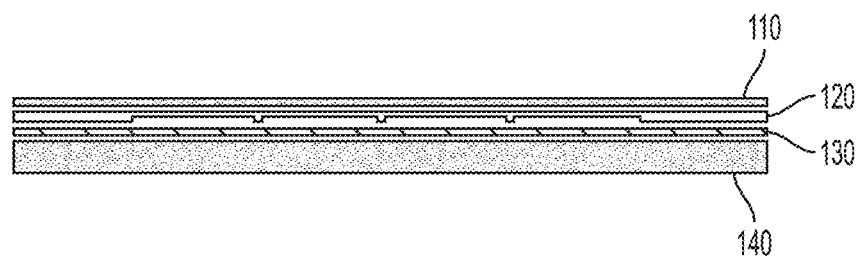
FIG. 2 shows a section view of the embodiment of FIG. 1.

Referring initially to FIGS. 1-2, an exemplary embodiment of a device 100 configured as a thin film sensor comprises a diaphragm 110, a chamber structure 120, an adhesive 130 and a substrate 140. In the embodiment shown, diaphragm 110 is configured as a thin film diaphragm transducer between 10 µm and 20 µm thick and is bonded to substrate 140 via adhesive 130. In particular embodiments, diaphragm 110 is approximately 15 µm thick and substrate 140 is approximately 50 µm thick. In the present disclosure, the thickness of a material is measured across the primary plane of the material (i.e. the minimum dimension for a given layer of material, as would be measured in a vertical direction in the configuration shown in FIG. 2).

In the illustrated embodiment, chamber structure 120 comprises a bonding pad 125 around its perimeter and chamber structure 120 is positioned between diaphragm 110 and substrate 140. In exemplary embodiments of device 100, substrate 140 can be electrically conductive, and in certain embodiments can be configured as an antenna.

Exemplary embodiments of device 100 may be fabricated by constructing a thin sensing film, which comprises of an array of diaphragms 110 enclosed by bonding pads 125. In certain embodiments, to construct the sensing film, multiple layers of photolithography with various polyimides can be performed on a carrier substrate. The diaphragm can be defined in one step, the chamber walls can be defined in a second step, and a thin adhesive film applied in a third step. The sensing film can then be released from the carrier.

In exemplary fabrication techniques, the sensing film can then be bonded to the substrate of choice. In certain embodiments, the thin adhesive can be deposited onto a conductive substrate. If the substrate is not inherently conductive, a thin conductive film may be deposited to provide a bottom electrode of the diaphragm sensor. The sensing film can then be bonded to the substrate under pressure and temperature.

In certain embodiments, the final fabrication step is to sputter an electrode and bond lead wires. For example, a thin conductive film can be deposited on top of the sensing film to define the top electrode of the diaphragm sensor. Lead wires can then be bonded onto the top and bottom electrodes.

In certain embodiments of the sensor, the sensing film (e.g. diaphragm 110) is 10-15 µm thick and substrate 140 is 50 µm thick stainless steel. In certain embodiments, diaphragms 110 form a sensing film that is 3 mm×10 mm, but it can be of arbitrary size to suit the application.

In certain embodiments, substrate 140 may be formed by polymers processing techniques. Other microfabrication techniques could produce a similarly-structured device composed of other materials, including traditional microfabrication ceramics such as silicon, silica, quartz, silicon nitrides, other nitrides, other oxides, and other insulating or semiconducting materials.

Figure 3:
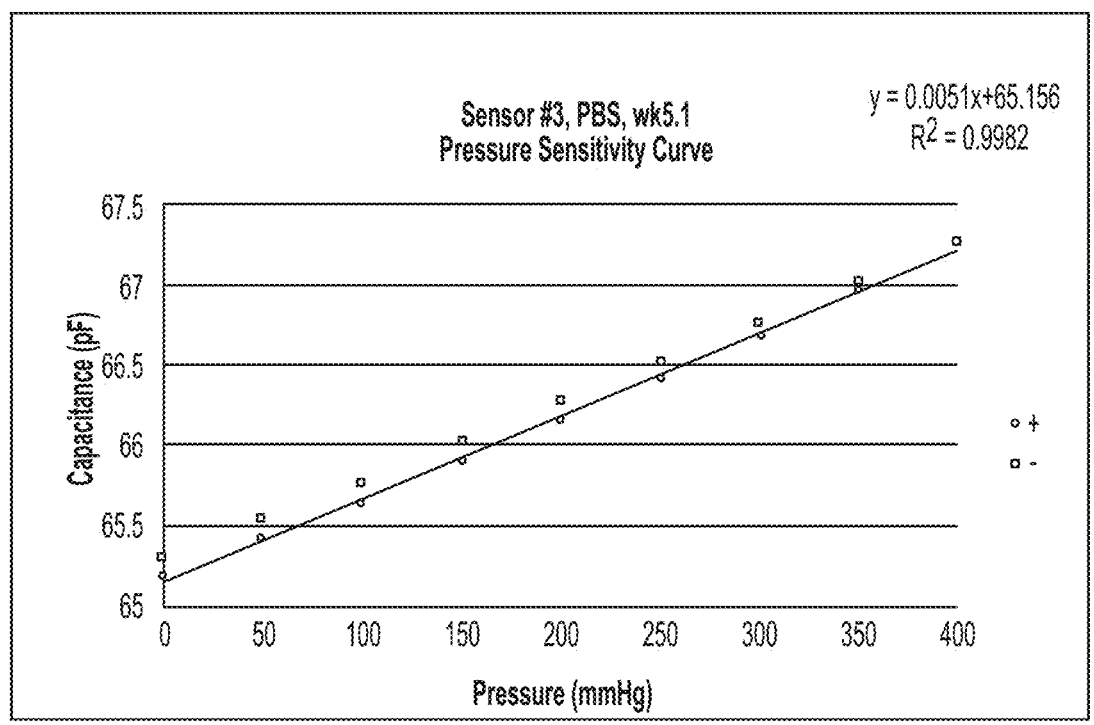
FIG. 3 shows a graph of capacitance versus pressure for one embodiment of a device according to the present disclosure.
Figure 4:
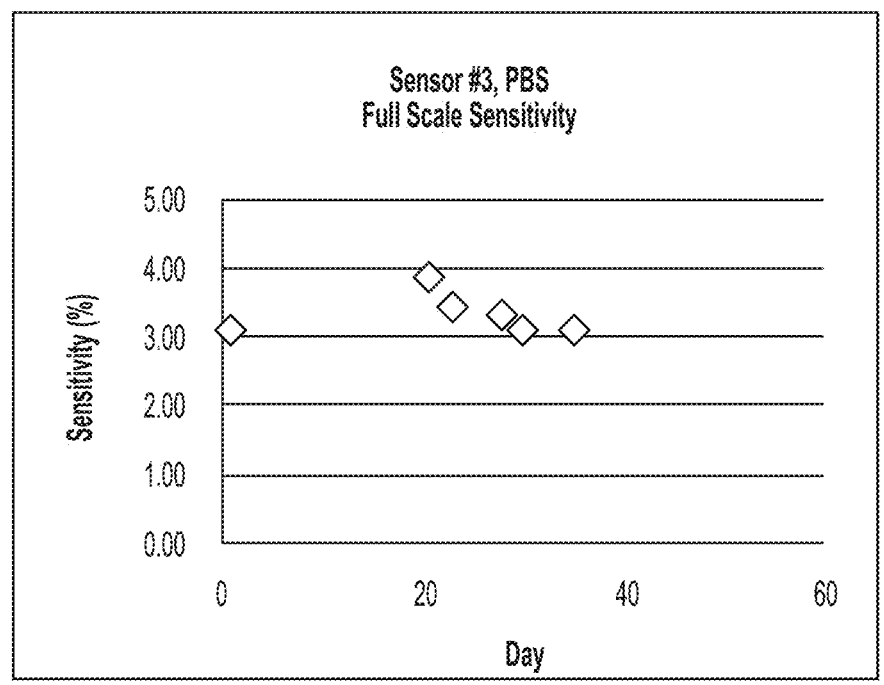
FIGS. 4-9 illustrate properties of the embodiment of FIG. 3 as measured over period of several days.
Figure 5:
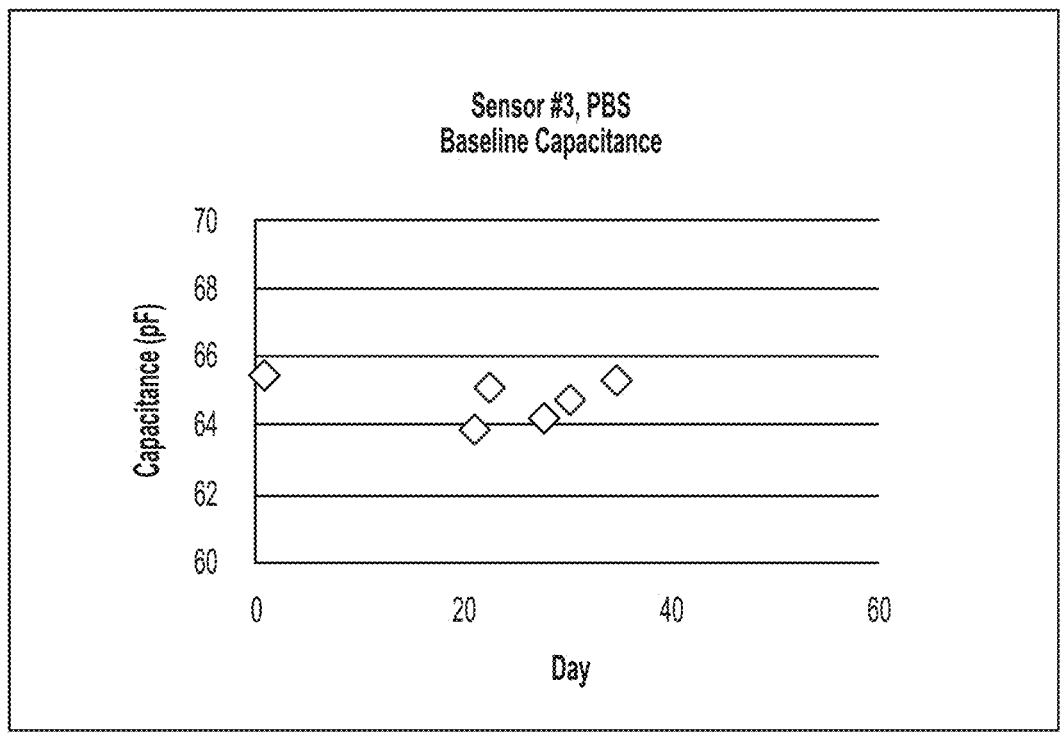
Figure 6:
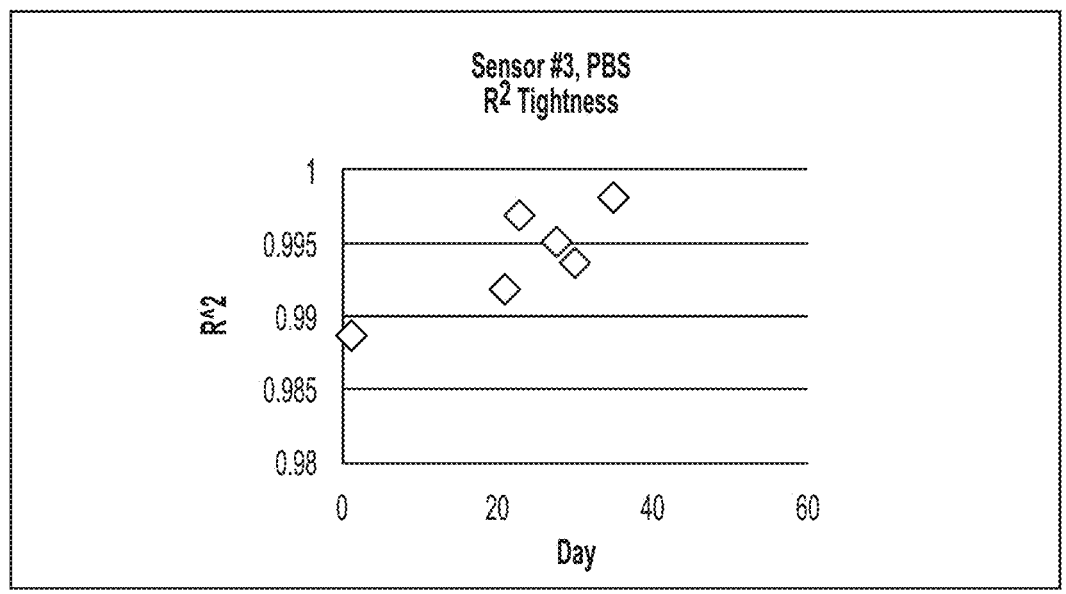
Figure 7:
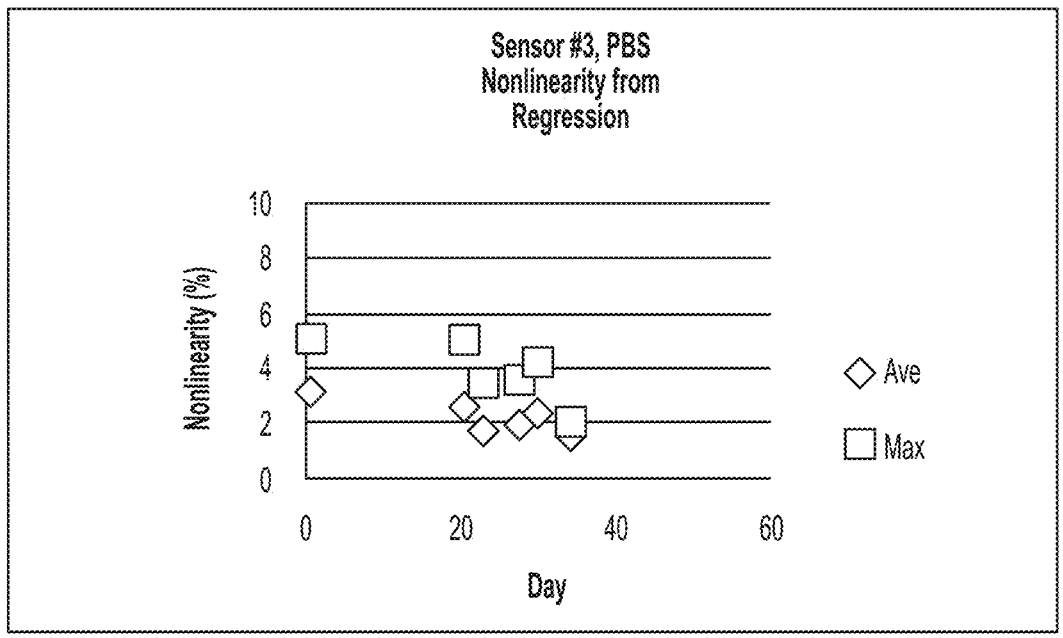
Figure 8:
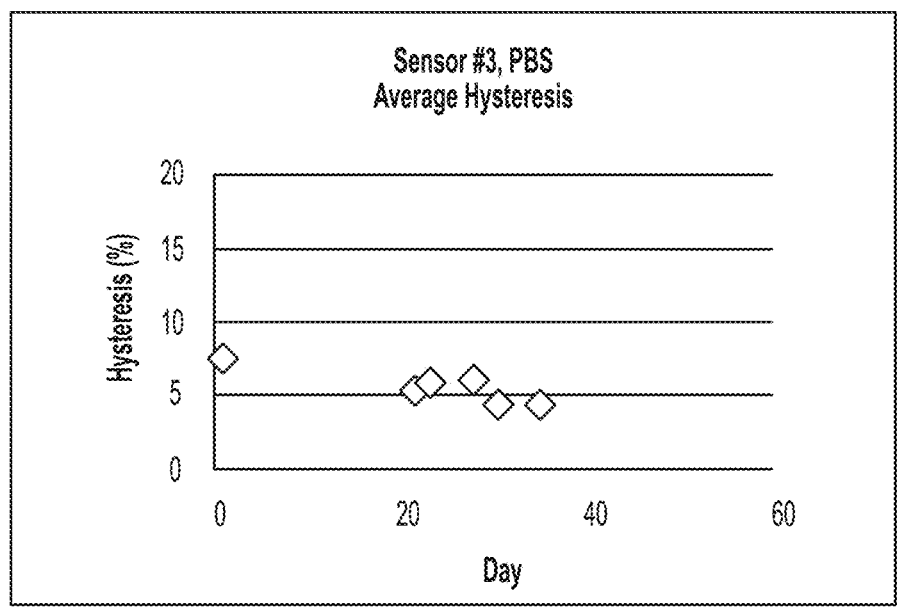
Figure 9:
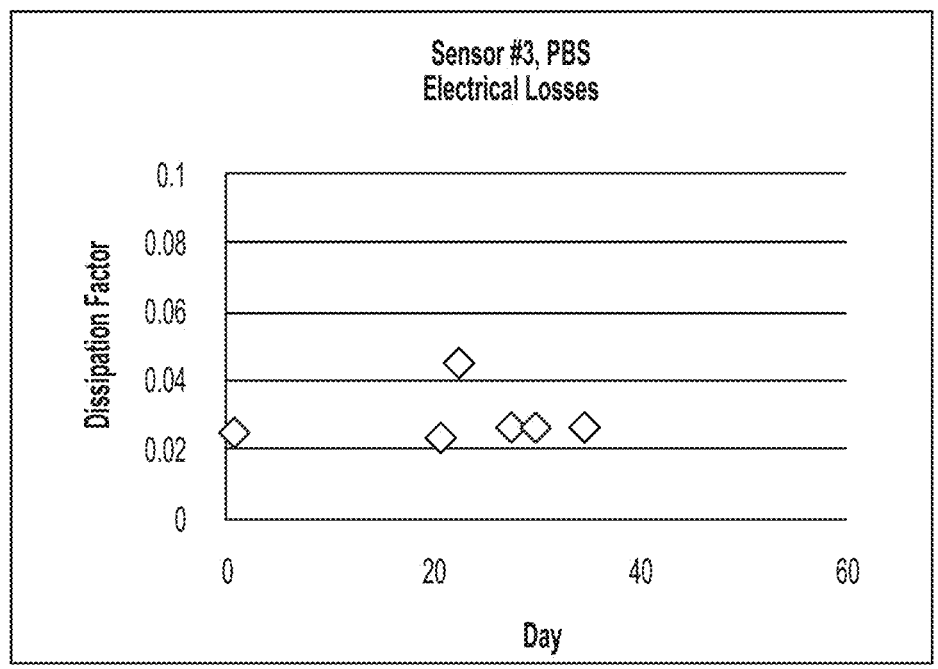
Figure 10:
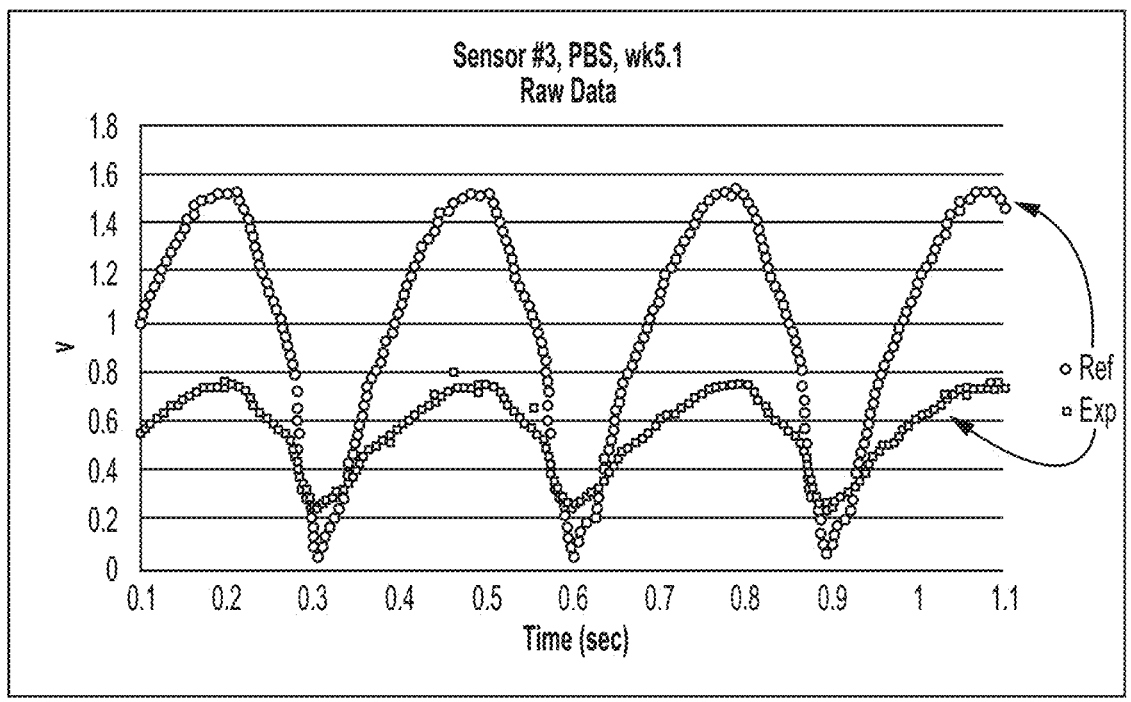
FIGS. 10-11 illustrate measurements of the embodiment of FIG. 3 of dynamic signals from inside a flow loop with pulsatile pressure.
Figure 11:
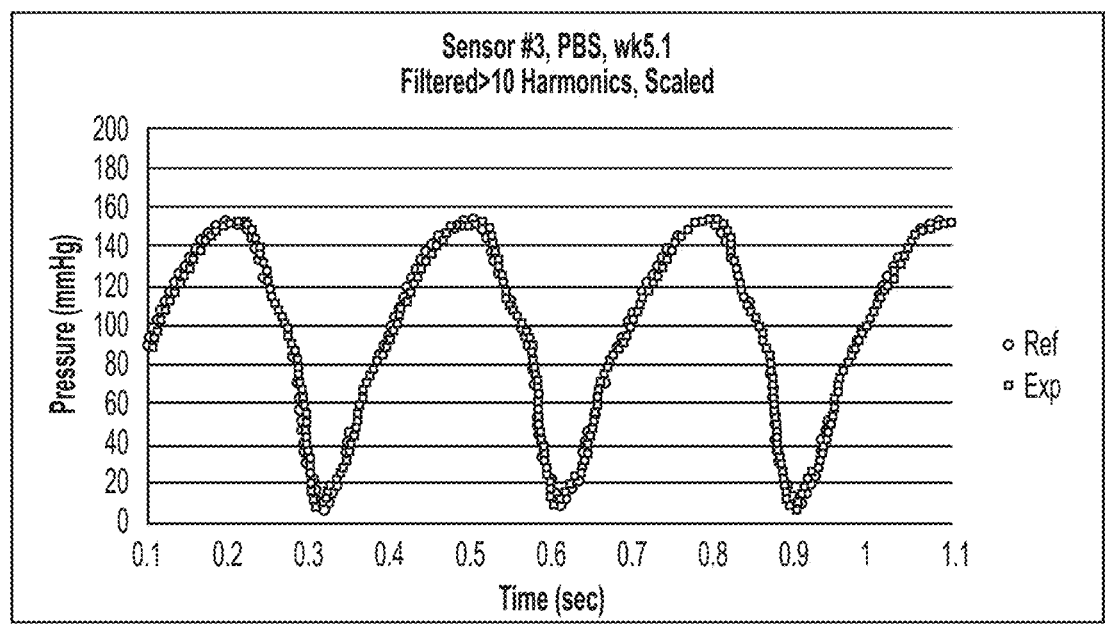

During operation of device 100, deflection of diaphragm 110 toward and away from substrate 140 can be measured by changes in electrical properties and correlated to environmental conditions or parameters affecting device 100. For example, in certain embodiments, the capacitance of device 100 (measured between diaphragm 110 and substrate 140) can be correlated to pressure. Referring now to FIG. 3, one example illustrates a substantially linear relationship between the measured capacitance (in pF) versus the pressure on diaphragm 110 (measured in mmHg). FIGS. 4-9 illustrate other properties of the embodiment of FIG. 3 as measured over period of several days. FIGS. 10 and 11 illustrate measurements of the embodiment of FIG. 3 of dynamic signals from inside a flow loop with pulsatile pressure. FIG. 10 illustrates waveforms from device 100 and a reference sensor. As illustrated, the average difference is approximately 1 mm Hg.

Figure 12:
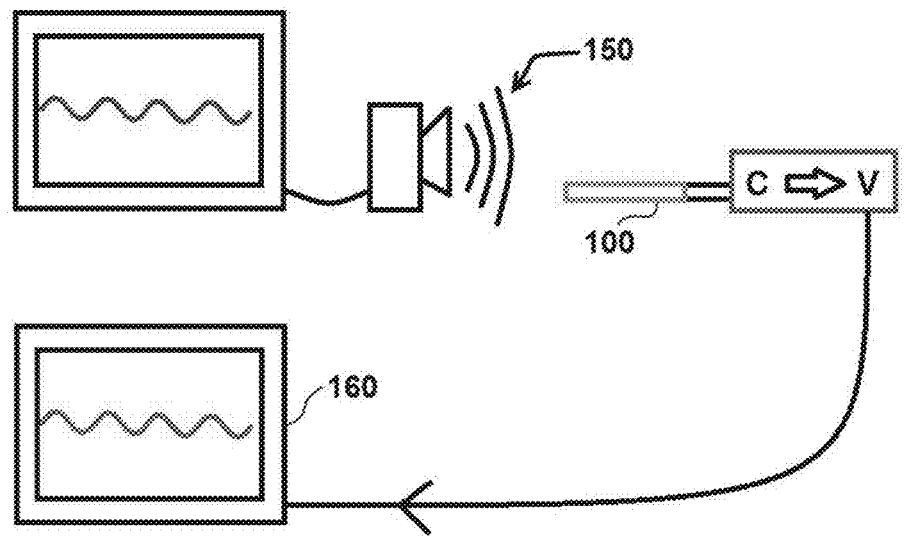
FIG. 12 shows a schematic of one embodiment of a device configured as an audio sensor.
Figure 13:
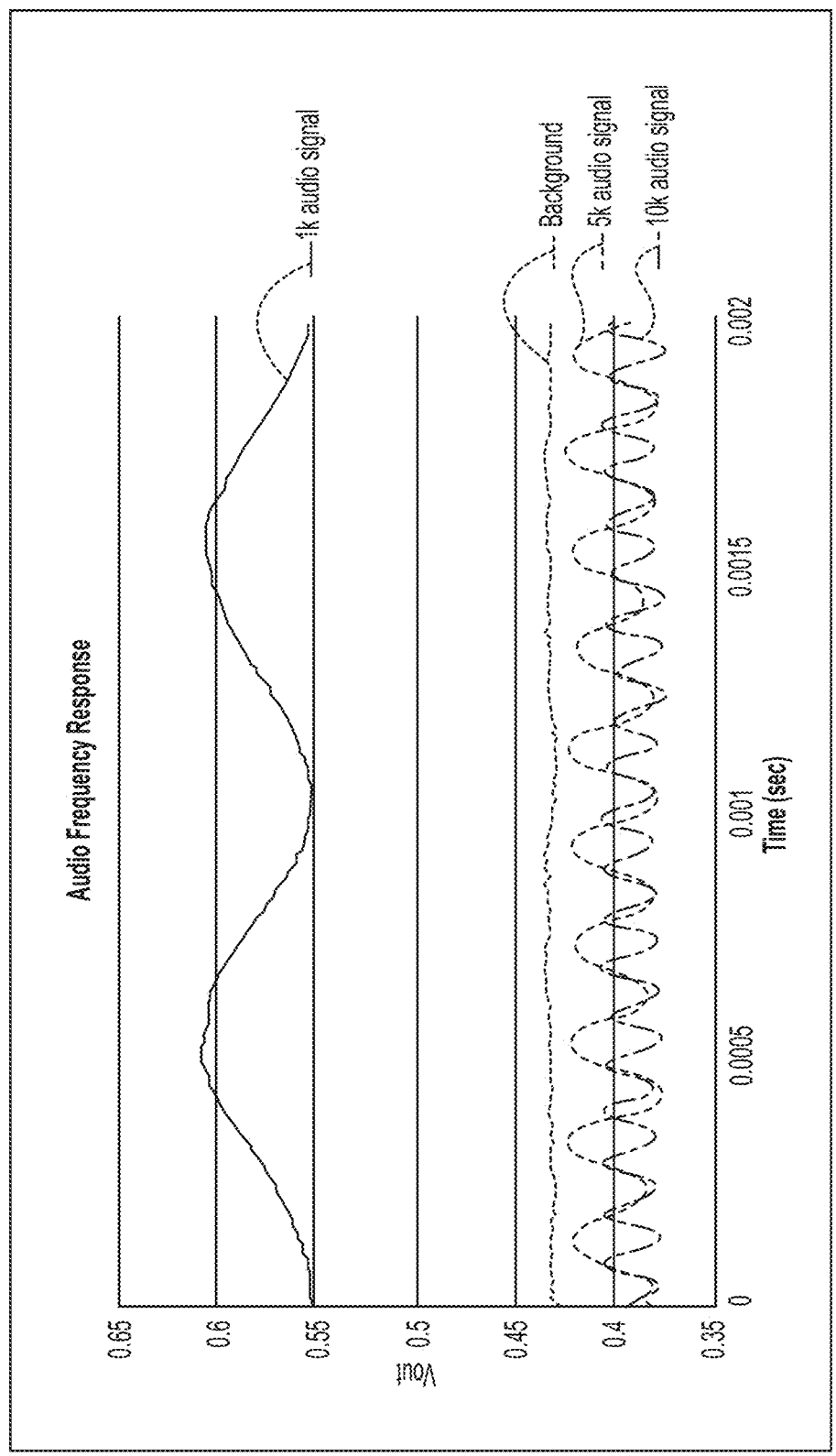
FIG. 13 shows data recorded with the embodiment of FIG. 16.

Referring now to FIGS. 12 and 13, a schematic of device 100 (and resulting data) are shown for an embodiment configured as an audio sensor. In this embodiment, device 100 senses an audio wave 150, which causes deflection of diaphragm 110 (not labeled in FIG. 6 for purposes of clarity; see FIGS. 1 and 2 for view depicting diaphragm 110). Diaphragm 110 deflections cause a change in the measured capacitance/voltage across device 100, which can be viewed as a waveform on display 160.

In the graph shown in FIG. 13, audio frequencies were recorded with high fidelity up to 10 kHz, indicating certain embodiments of device 100 may be suitable for use for hearing aid implants. In addition, the ability to record frequencies up to 10 kHz also indicate the potential utility of device 100 in cardiovascular applications due to the ability to faithfully record high frequency information in the pressure waveform.

Device 100 can be used in many different applications. For example, device 100 can be configured for use as a sensor, including a pressure, acoustic, force or flow sensor. Device 100 may also be configured as a mechanical actuating device, including for example an electrostatically (or pneumatically)-driven membrane that can be used as a pump or valve in microfluidics applications. For example, in a valve configuration, diaphragm 110 can be deflected outward (e.g. away from substrate 140) to occlude flow and toward substrate 140 to allow flow to pass over diaphragm 110.

In still other embodiments, device 100 can be configured a capacitive microphone, including for example configuration a hearing aid.

In certain embodiments, device 100 can be configured as a chemical or biological sensor. For example, chamber structure 120 can be configured as a polymer or hydrogel with selective absorption that can swell and deflect diaphragm 110 in the presence of certain analytes.

In particular embodiments, device 100 may also be used for detecting chemical or biological analytes by mass loading of the sensing diaphragm, which changes its resonance frequency. The sensing diaphragm can have analyte receptors bound to its surface and the resonance frequency of the sensing diaphragm can be monitored by actuating device 100 electrostatically or thermally. Detection of the analyte occurs by recording the shift in resonant frequency of the diaphragm.

In specific embodiments, device 100 may be configured for indirect sensing by principles similar to those used in a Golay cell. For example, chamber structure 120 may be filled with a gas that expands with increased temperature and causes deflection of diaphragm 110. In particular embodiments, diaphragm 110 may be coated with a bandpass filter to provide for specific detection of light wavelengths or color. Such configurations could be used in imaging or retinal implant applications.

In certain embodiments, device 100 can be configured as a thin-film pressure sensor in an inductor-capacitor (LC) resonator for a wireless implantable blood pressure sensor. In particular embodiments, device 100 can operate by capacitive, resistive, and resonant mechanisms. In exemplary embodiments, device 100 can sense a broad range of factors, individually and multiple simultaneously. Device 100 can be configured as an electrical inductor-capacitor (LC) resonator that measures pressure by a thin film capacitive transducer that resonates with a stent-like antenna.

In exemplary embodiments, the thin active region of the sensor is decoupled from a thick inactive substrate. Certain embodiments can incorporate the use of a shape-memory NiTi as an antenna for percutaneous catheter delivery of the device. In certain embodiments, movements in local pressure change the transducer capacitance and thus shift the resonance frequency. In particular embodiments, the resonance frequency can be monitored externally by magnetic coupling to determine intravascular pressure.

In specific embodiments, the sensor can be bonded to a thin metallic substrate and coupled to a flexible NiTi stent-antenna (inductor), and the diaphragm sensor and inductive antenna form an electrical inductor-capacitor (LC) resonator.

In certain exemplary embodiments, device 100 has a thin profile, is wireless, biocompatible, implantable, and allows for intravascular implantation for blood pressure sensing. In particular embodiments, device 100 can be fabricated with biocompatible materials, is flexible and due to thin profile allows for 3-D conformations of sensor in vivo, allows for implementation in medium to small arteries, including the peripheral arteries.

In particular embodiments, device 100 can be bonded to virtually any substrate, and be integrated or embedded into various devices. The thin and flexible profile of device 100 is suitable for implantation into constrained spaces which were previously inaccessible for sensors.

The replacement of a thick silicon wafer onto which most pressure sensors are built with a very thin substrate (or the surface of an existing device or implant, including e.g. a stent) can save hundreds of micrometers of thickness which can be critical in particular applications. For example, one embodiment enables the development of a wireless resonant pressure sensor which is suitable for implantation in a large, medium, or small sized artery. As described in the literature reviews on endovascular blood pressure sensing devices and on pressure transducers, transducer size has been a limiting factor in the development of small implantable devices.

As described previously, exemplary embodiments of the present disclosure substitute the platform for the sensing diaphragm to reduce sensor thickness. Commercially available pressure sensors use silicon wafer as substrates with a thickness of about 500 µm, most of which can be eliminated by integrating the sensing element onto a robust surface of the device.

Test Data

Figure 26:
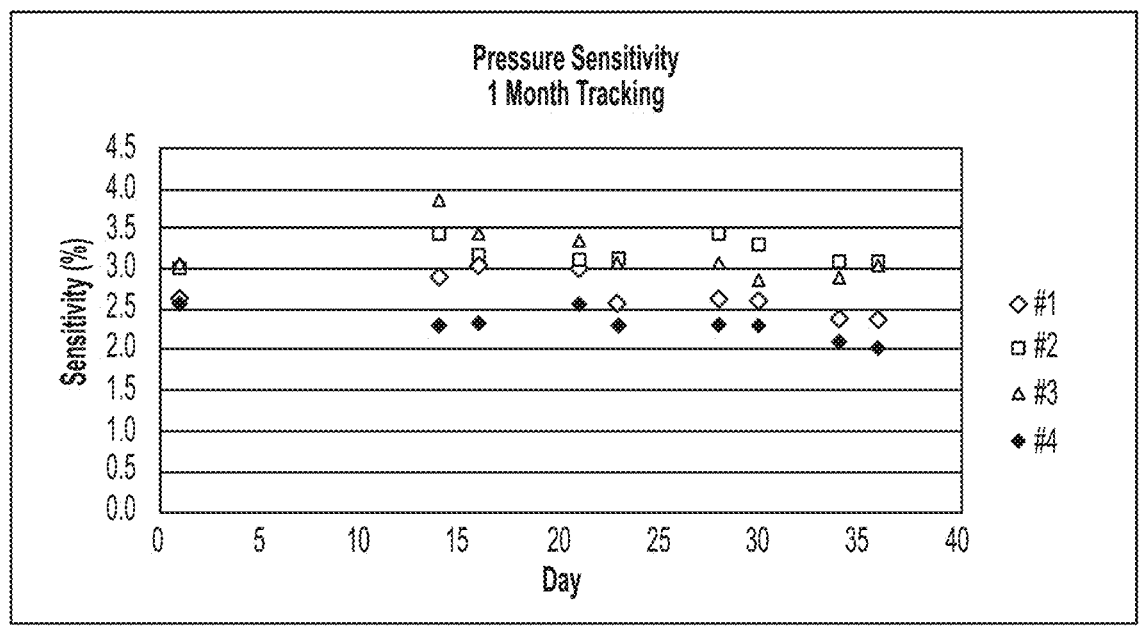
FIGS. 26-28 illustrate data for exemplary embodiments of four sensors according to the present disclosure over one month in saline under pulsatile pressure.
Figure 27:
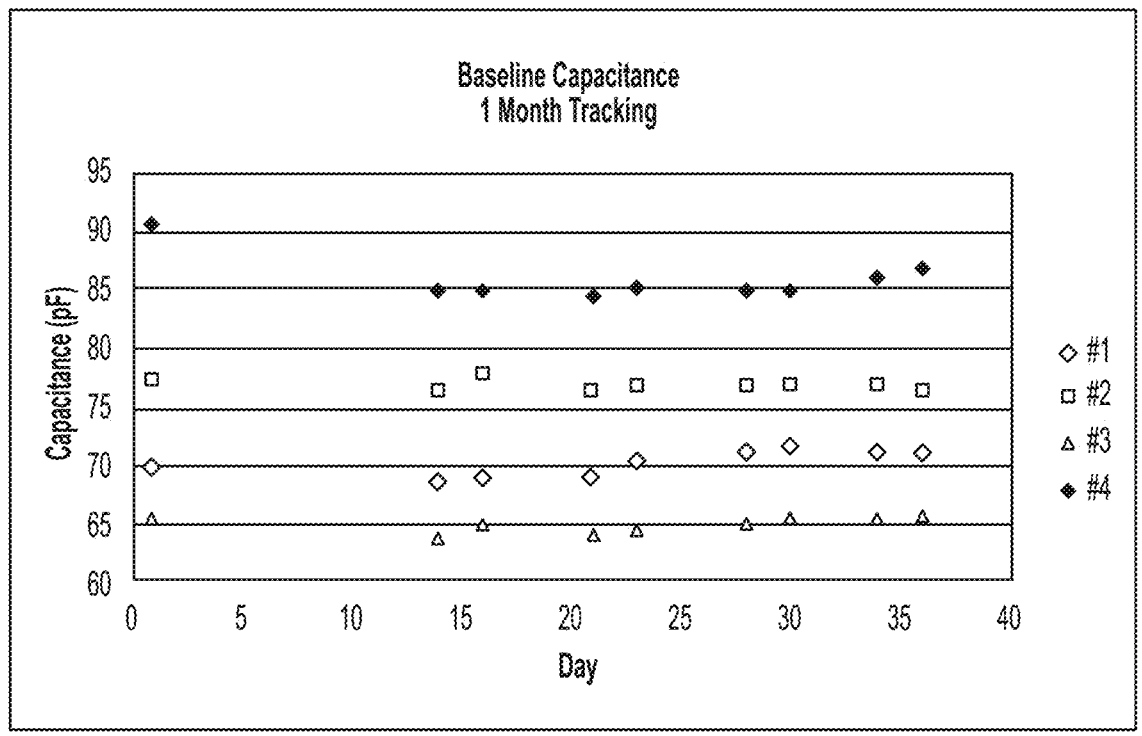
Figure 28:
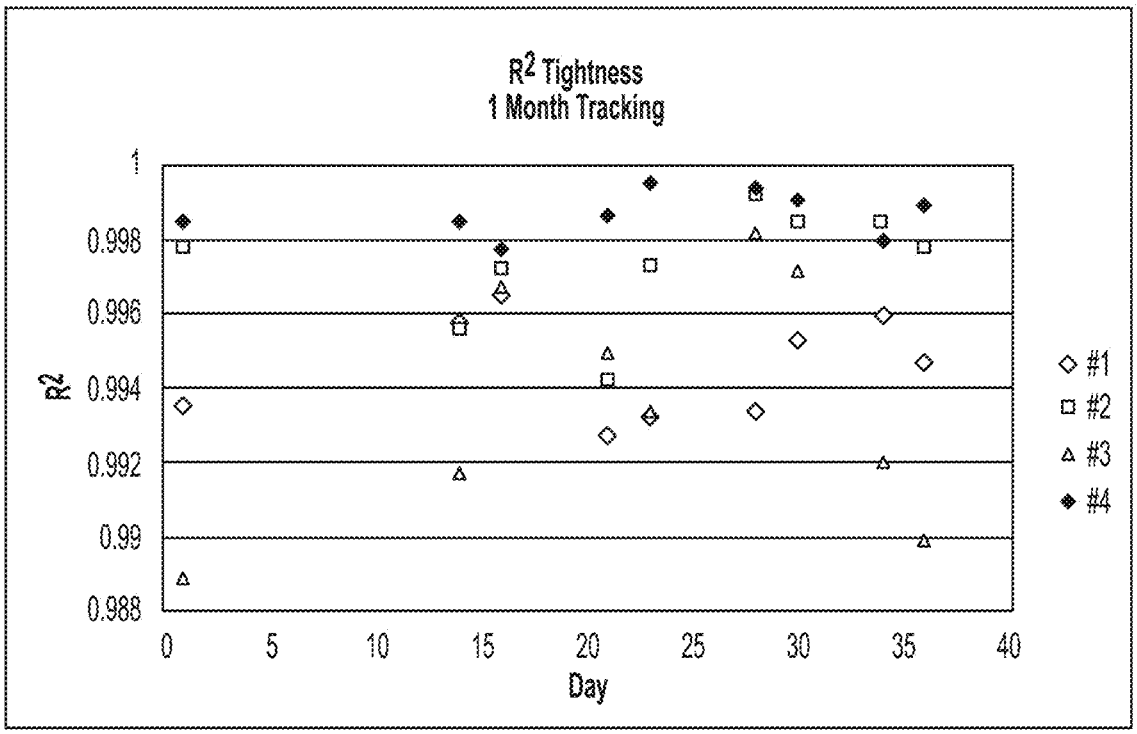
Figure 29:
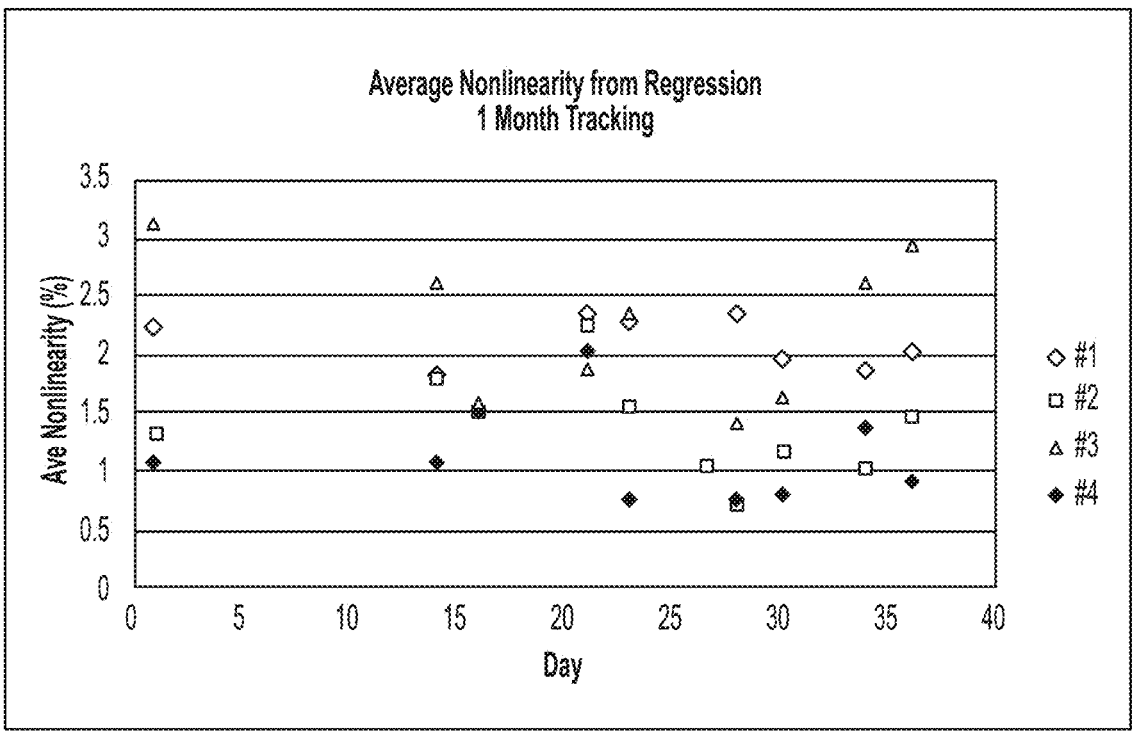
FIGS. 29-32 contain regressions and drift of parameters over the one month period for the data illustrated in FIGS. 26-28.
Figure 30:
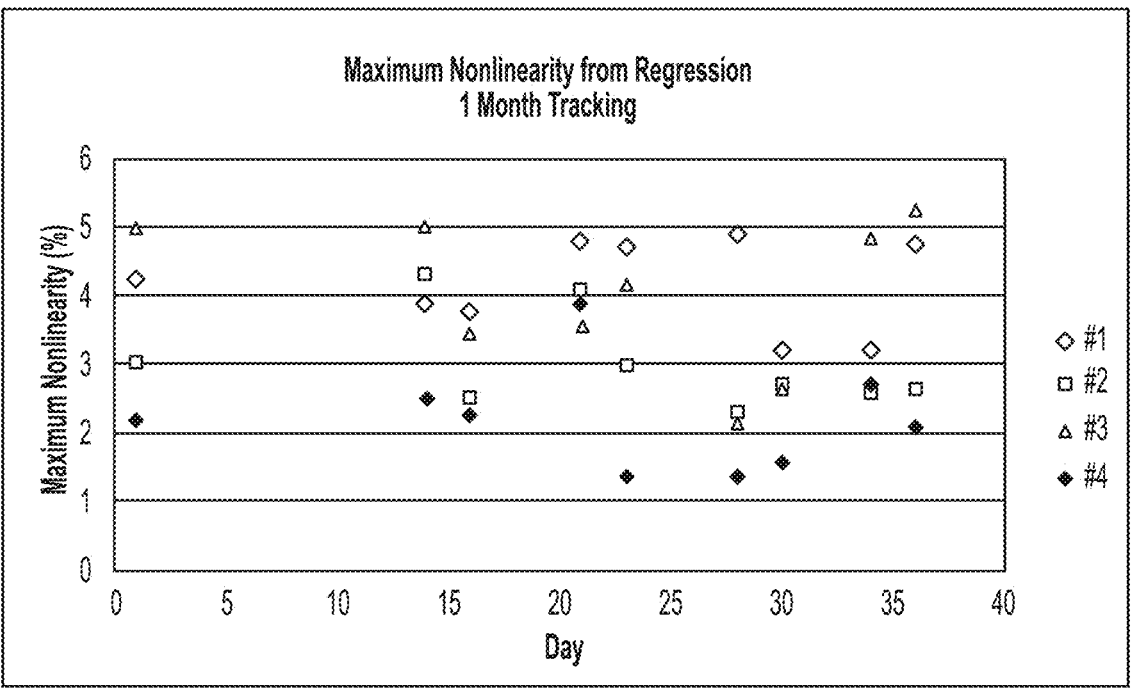
Figure 31:
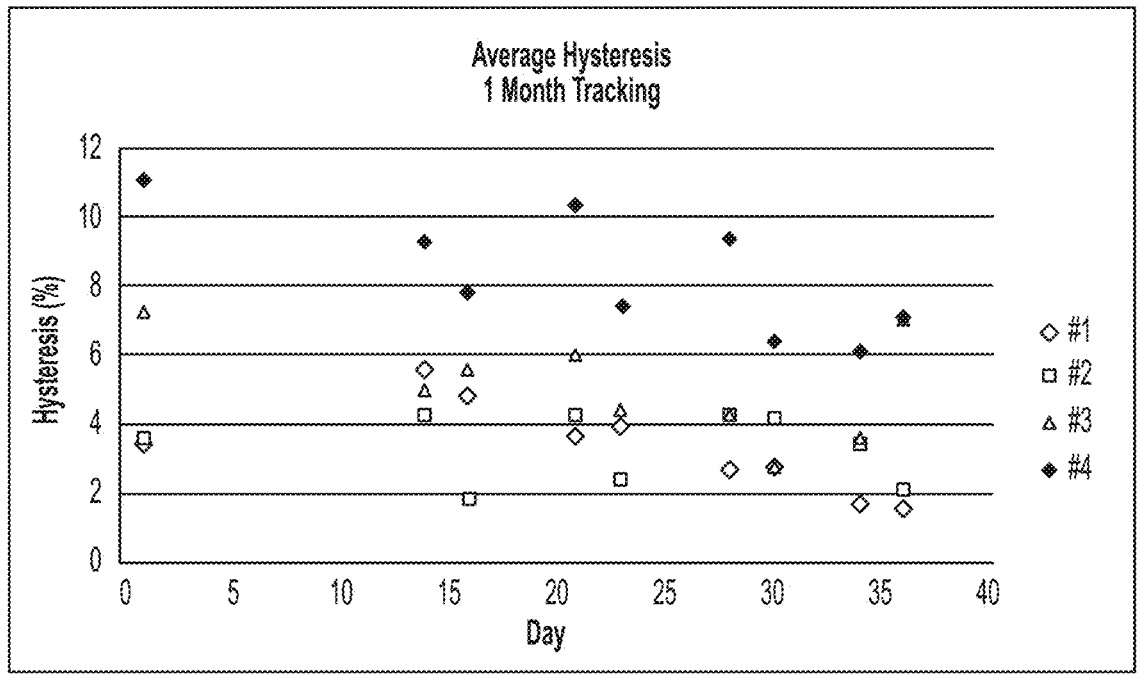
Figure 32:
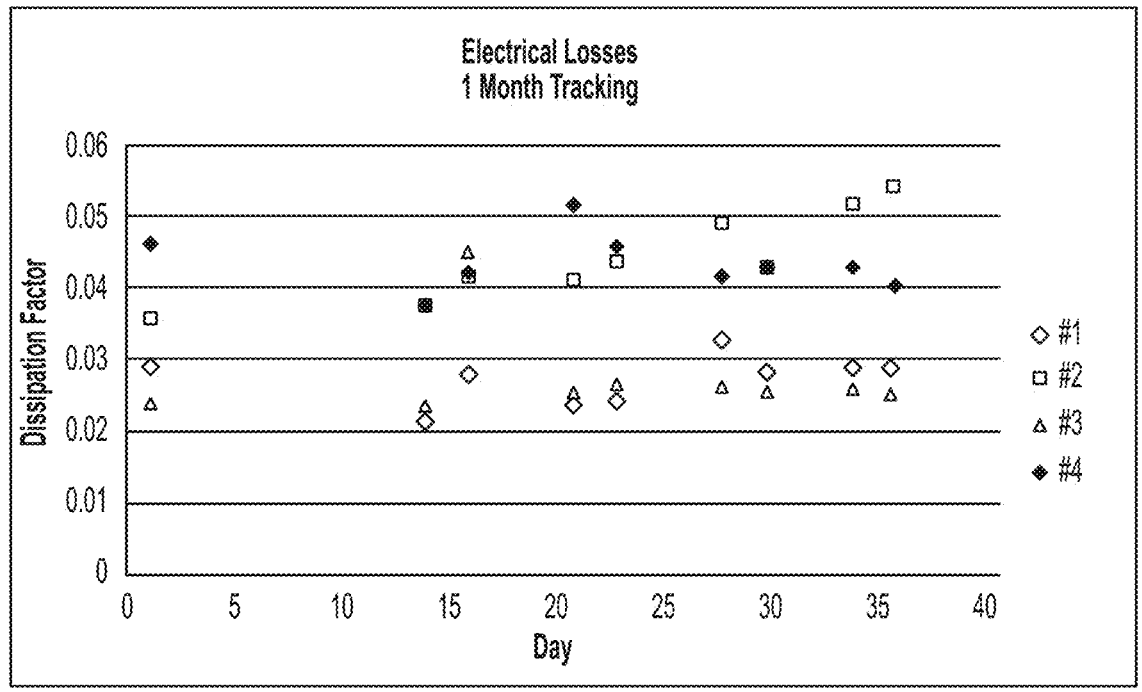
Figure 33:
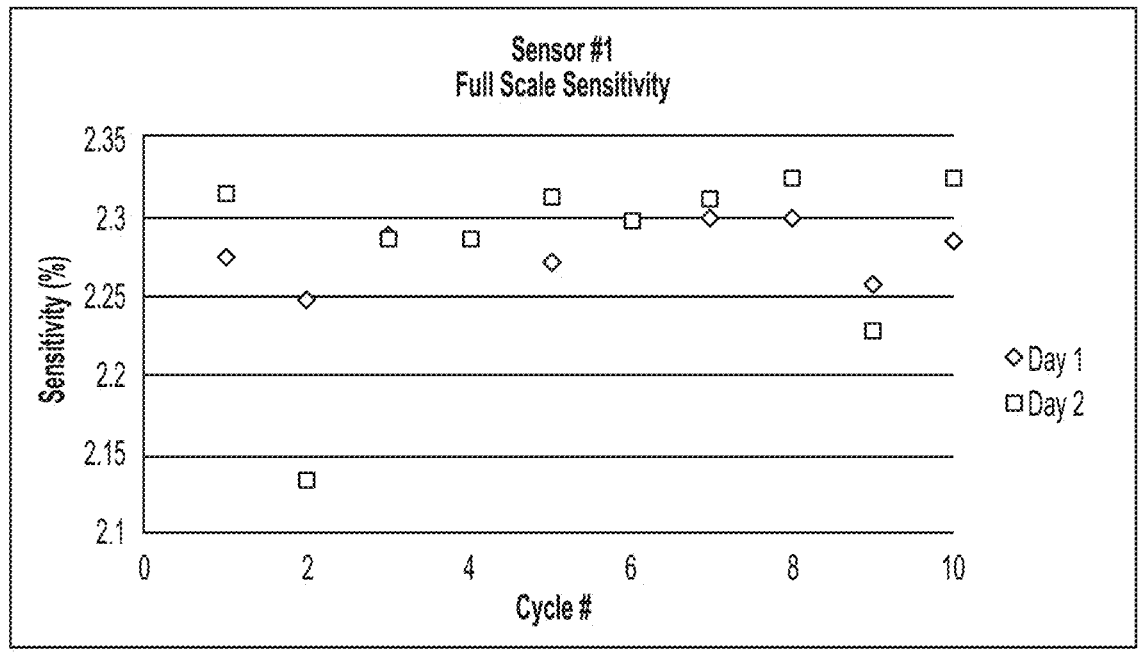
FIGS. 33-39 contain data from one sensor which addresses the source of drift in the parameters for the data illustrated in FIGS. 29-32.
Figure 34:
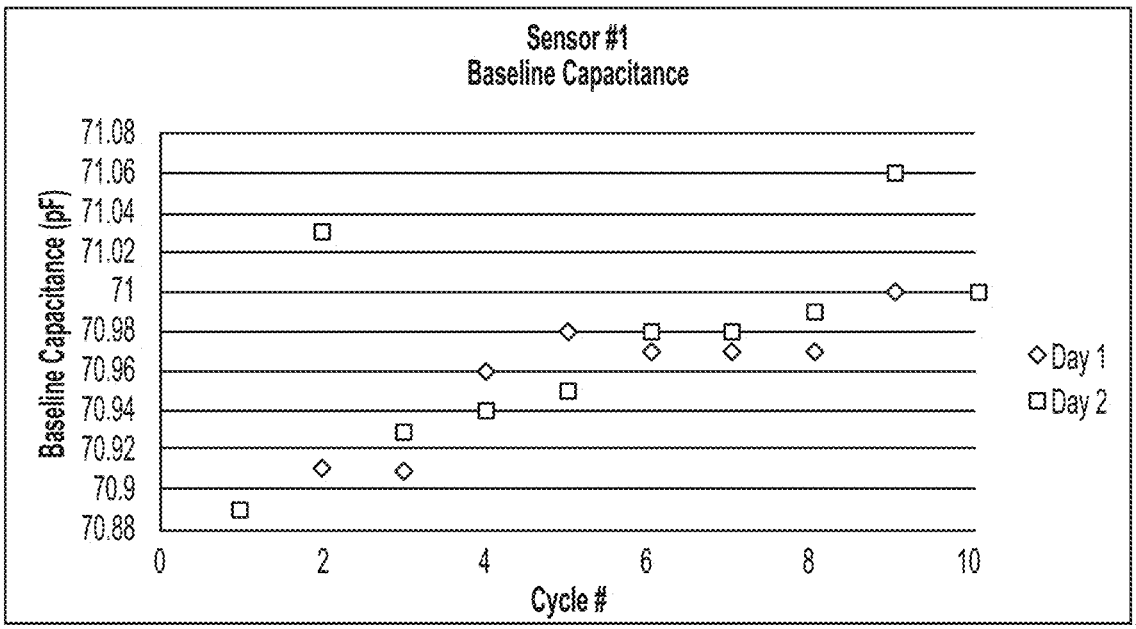
Figure 35:
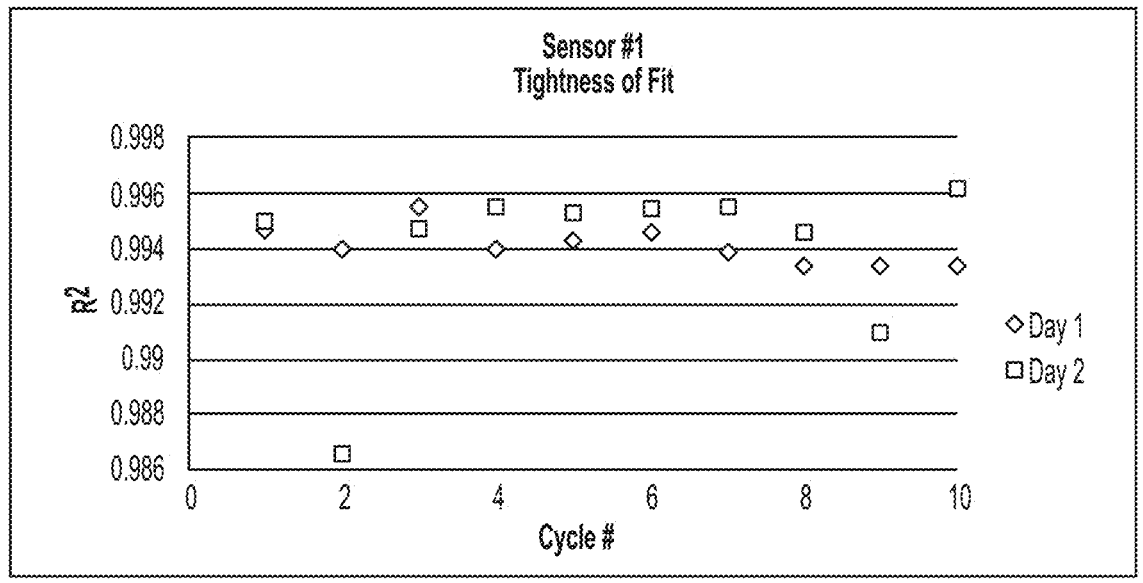
Figure 36:
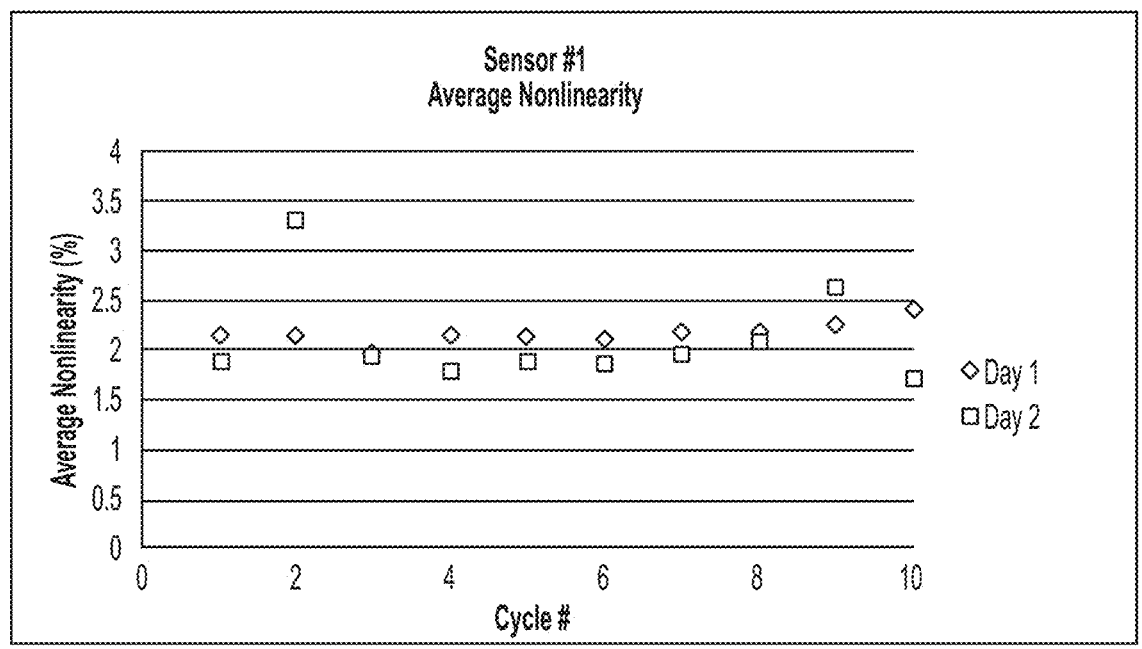
Figure 37:
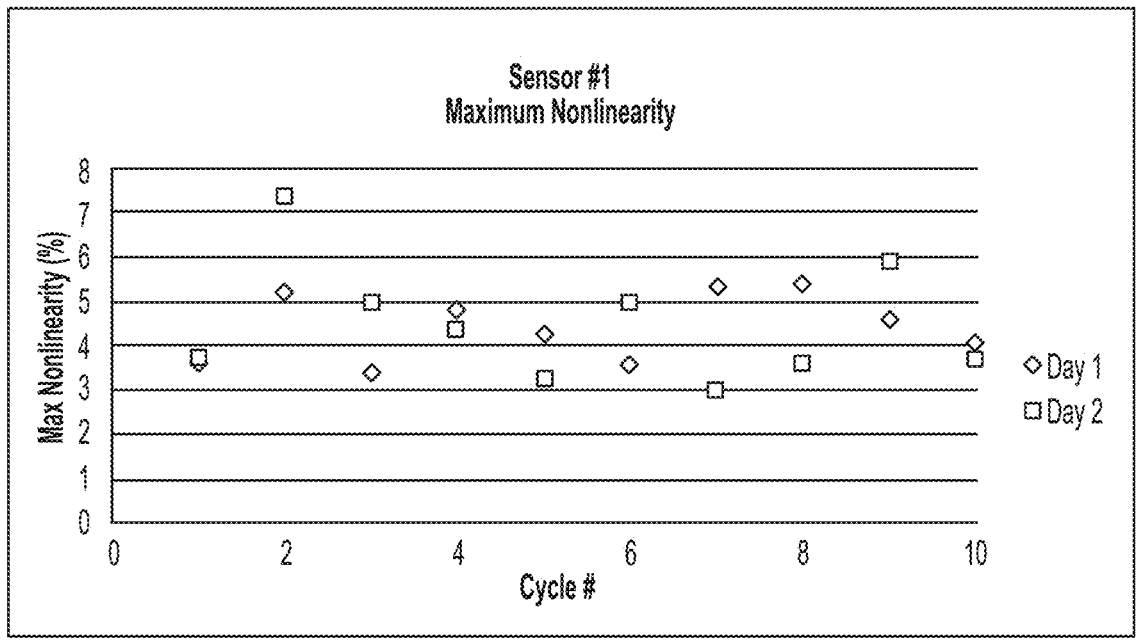
Figure 38:
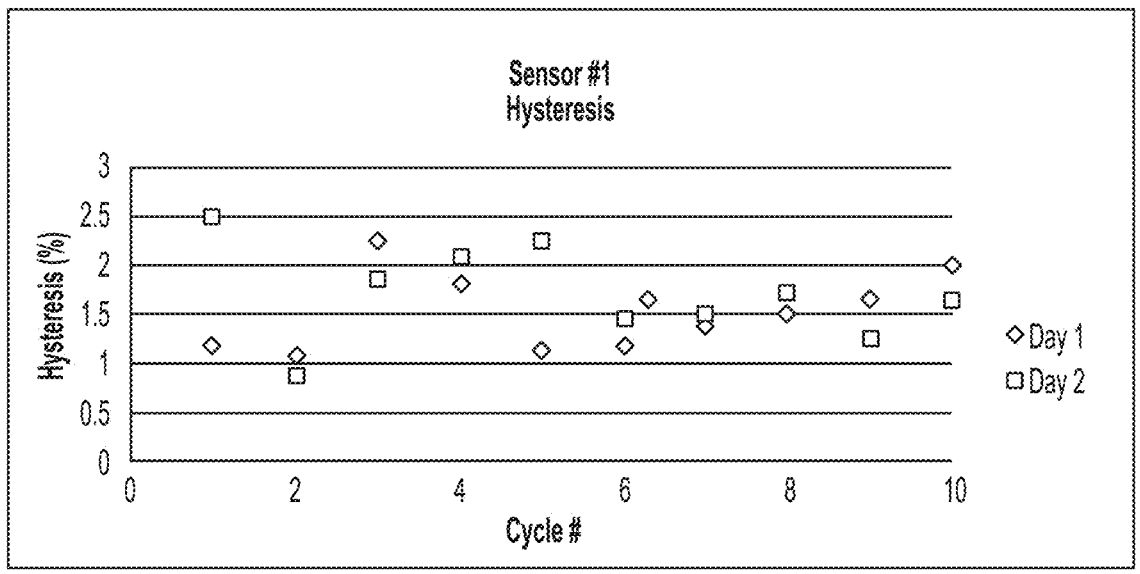
Figure 39:
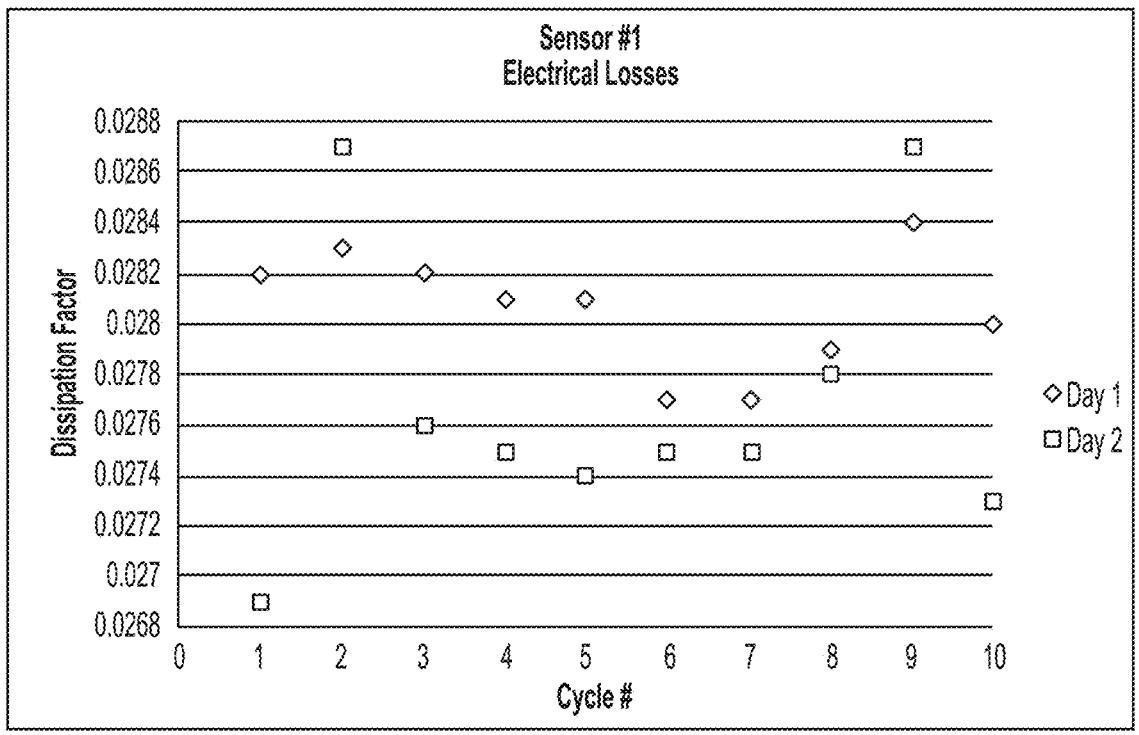

FIGS. 26-28 provide raw data on four sensors over one month in saline under pulsatile pressure. The data includes all tracked parameters, and the sensors had an initial two week immersion period in saline to allow parameter values to settle. Those values were then measured two times per week.

FIGS. 29-32 contain regressions and drift of parameters over the one month period. A graph at the end shows average drift in each parameter.

FIGS. 33-39 contain data from one sensor which addresses the source of drift in the parameters. Pressure was increased to 400 mmHg and pressure sensitivity curves were recorded; this was repeated for ten consecutive cycles. Some drift in sensor parameters are noted (for instance, 0.15% increase in baseline capacitance). The sensor was left alone for a twelve hour break, and then ten more cycles were performed. For almost all of the parameters, after the twelve hour break, the parameter value returned to the original value from day one, indicating that the drift in parameters was not permanent (e.g., a hysteresis effect which can be addressed during development and commercial design).

Design and fabrication of exemplary embodiments requires detailed knowledge and synthesis of multiple fields including microelectronics, microfabrication, cardiovascular medicine, and biomaterials. Additionally, silicon wafers are the epicenter of the microelectronics and microfabrication fields; departing from this fabrication orthodoxy is difficult.

Figure 14:
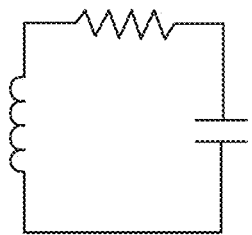
FIGS. 14-25 show circuits and data for a specific embodiment for insole pressure measurement.
Figure 14:
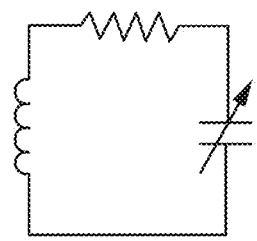
Figure 14:
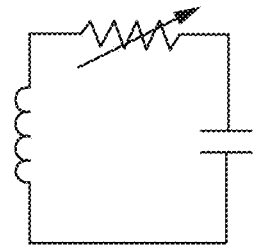
Figure 14:
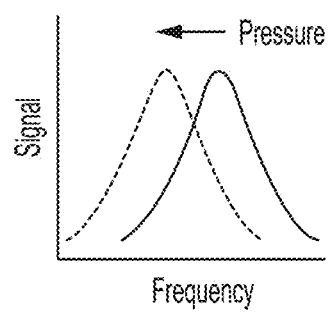
Figure 14:
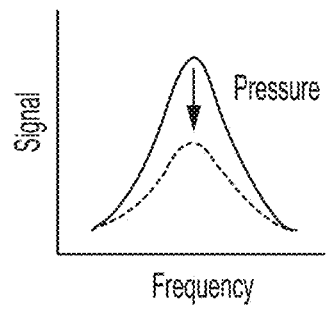

Embodiments of the current invention include a class of resonant sensors which can be used in a shoe insole for monitoring foot pressures. The general sensor is a resistor-inductor-capacitor (RLC) resonant circuit, which allows for either capacitive sensing or resistive sensing. FIG. 14 shows circuit schematics of these two possible configurations. In both cases, an external device with a small coil and a radio link (e.g., Bluetooth), such as a clip on the outer shoe, an anklet, or a waist belt, can interrogate the sensor and transmit the pressure signals to a smart device, computer, or wireless network.

In the capacitive design, a planar conductive coil is electrically connected to a capacitive pressure transducer to form an RLC tank, which is then embedded into an insole. The resonance frequency of the tank depends on the applied pressure. The sensor can be interrogated by an external coil which sweeps across a specified frequency range to monitor shifts in the resonance frequency.

In the resistive design, a planar conductive coil is electrically connected to a capacitor and a resistive transducer to form an RLC tank, which is then embedded into an insole. In this case, the resonance frequency of the tank is fixed, but the quality of resonance (quality factor Q) depends on the applied pressure. The sensor can be interrogated by an external coil at a fixed frequency by monitoring the strength of the magnetically coupled signal.

Figure 15:
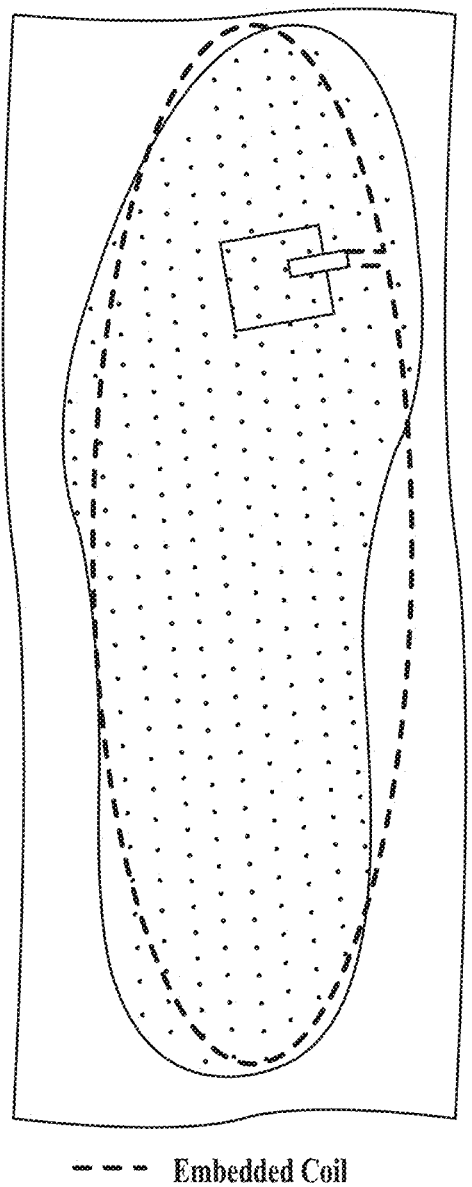
Figure 16:
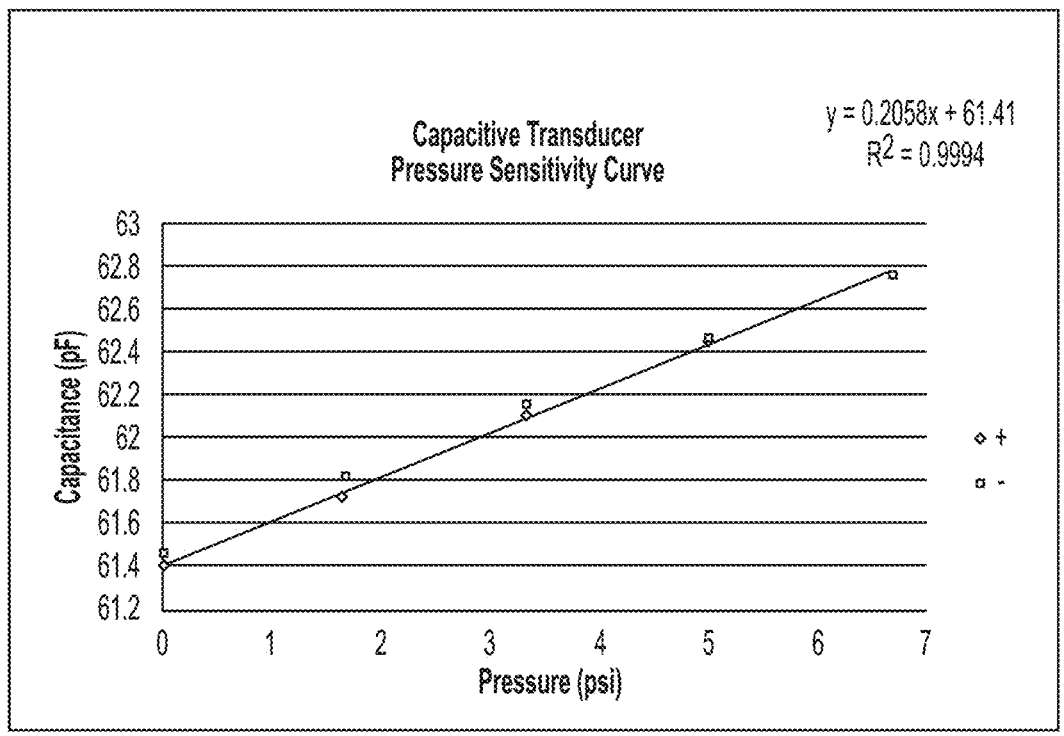

The capacitive design of an RLC sensor has been enabled. Referring back now to FIG. 15, a prototype insole is shown with a thin film capacitive transducer and an embedded 2-turn coil. The prototype has a strong and linear pressure sensitivity (40 kHz/PSI; R2=0.993). Further experimental data are attached in an appendix. A video of the sensor in operation will be sent electronically. The particular type of capacitive transducer is non-essential to the invention. A variety of thin transducers could easily be used, from capacitive microsensors to custom capacitive sensors made from a sandwich of thin metal foil with a compressible dielectric in the middle.

Figure 17:
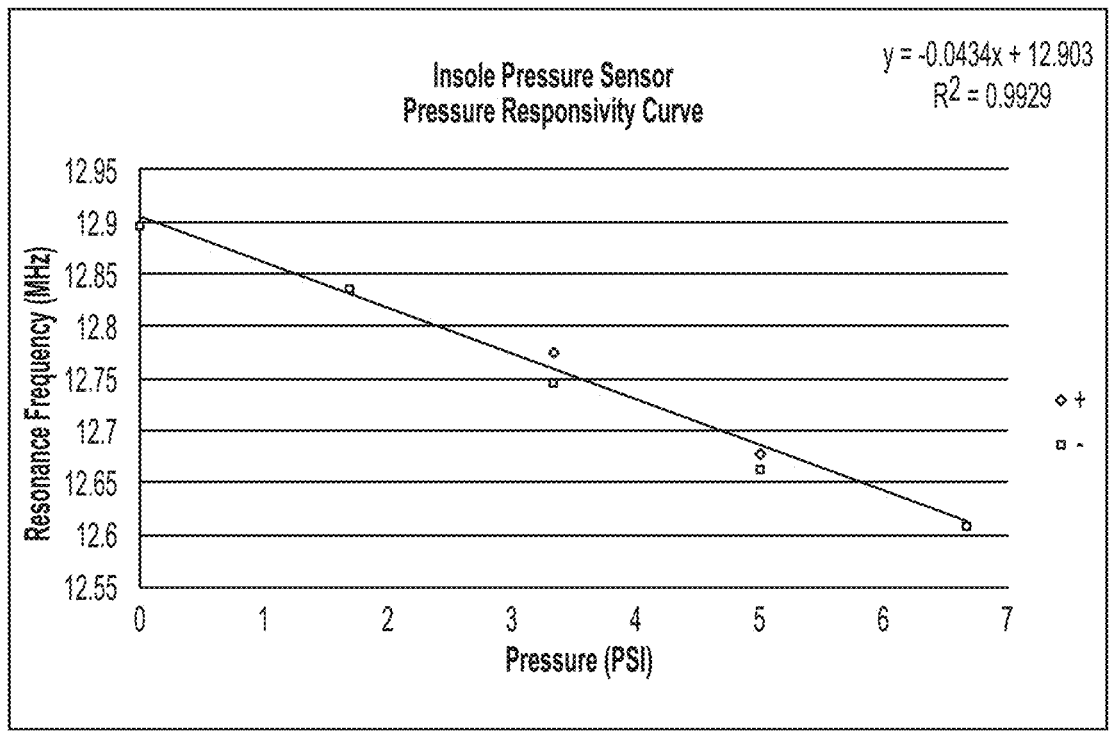
Figure 18:
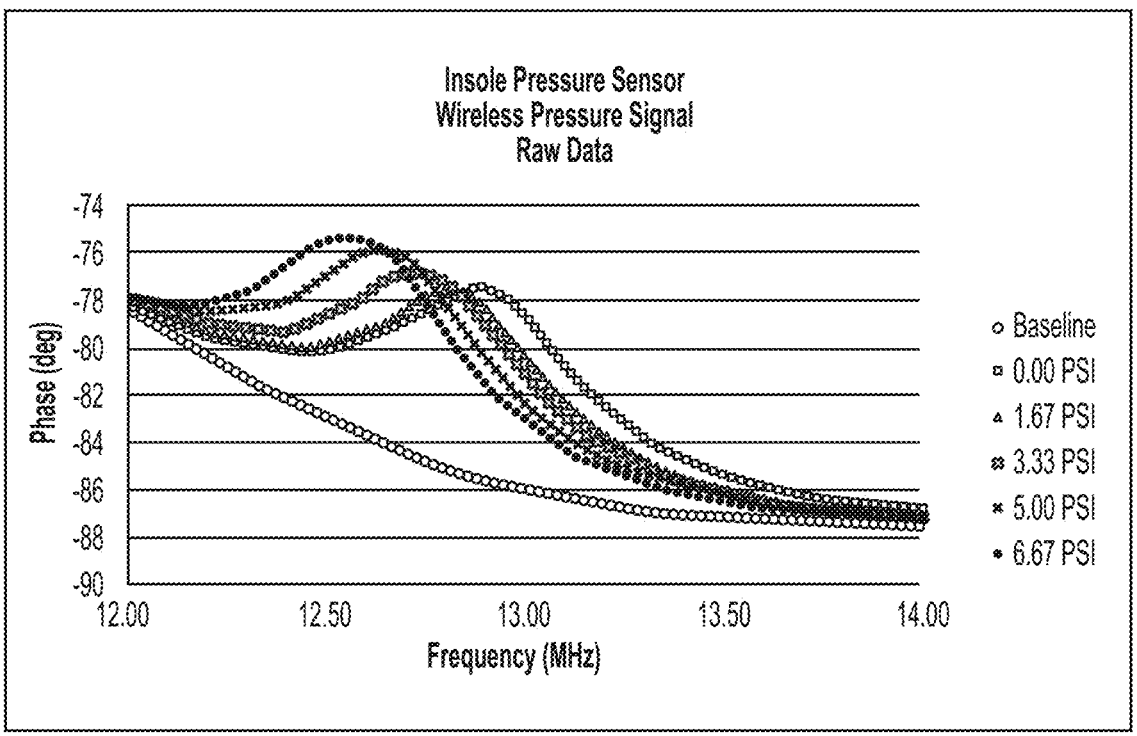
Figure 19:
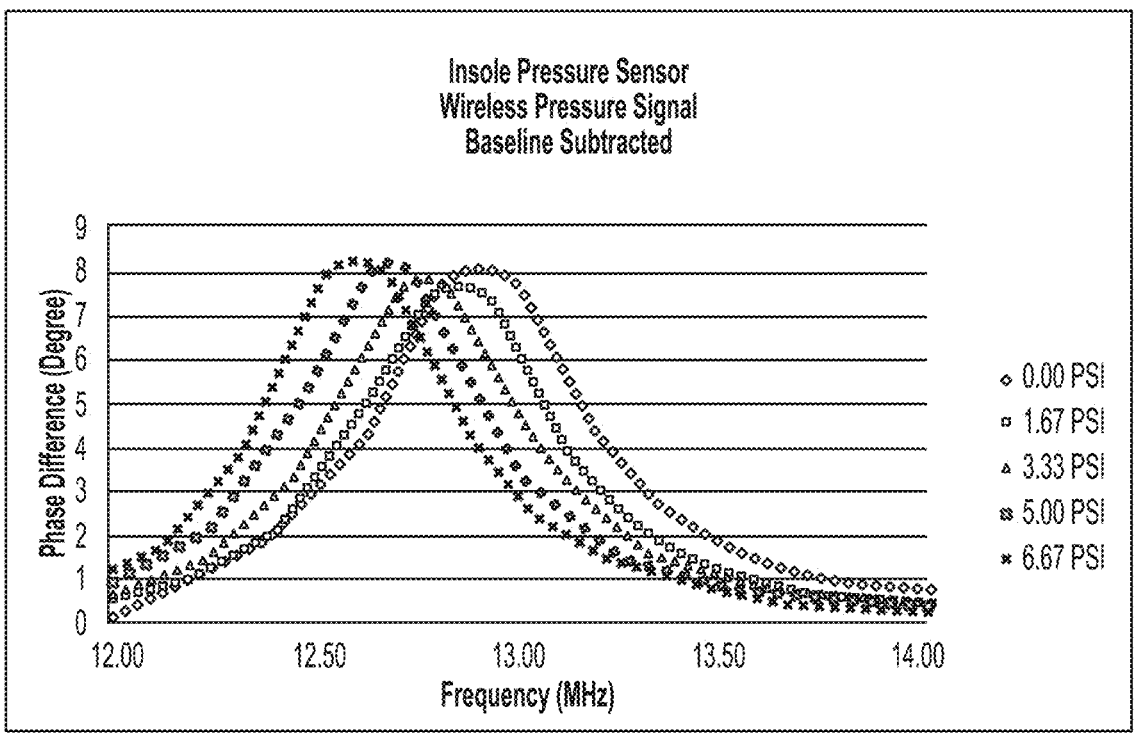
Figure 20:
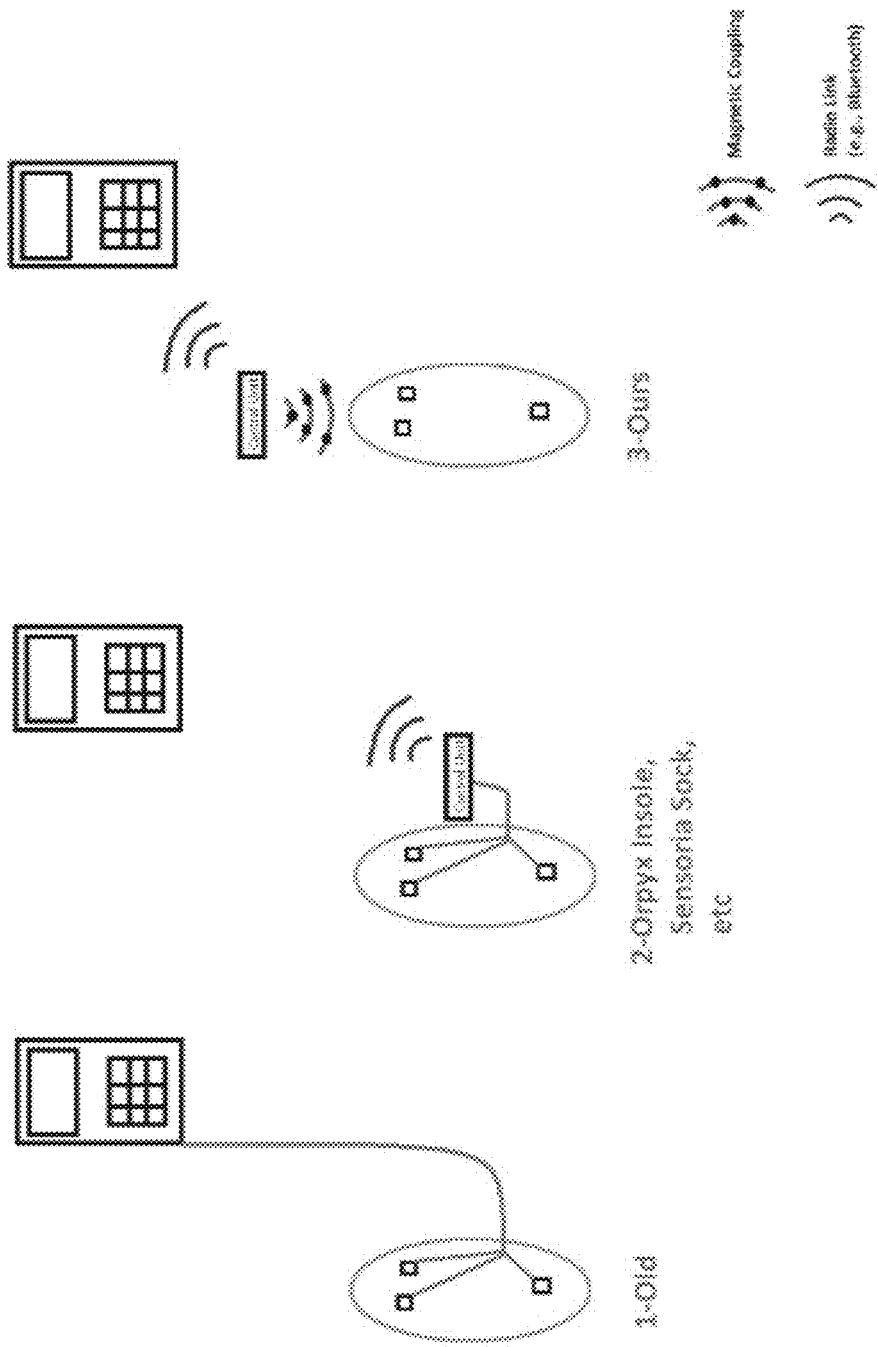
Figure 21:
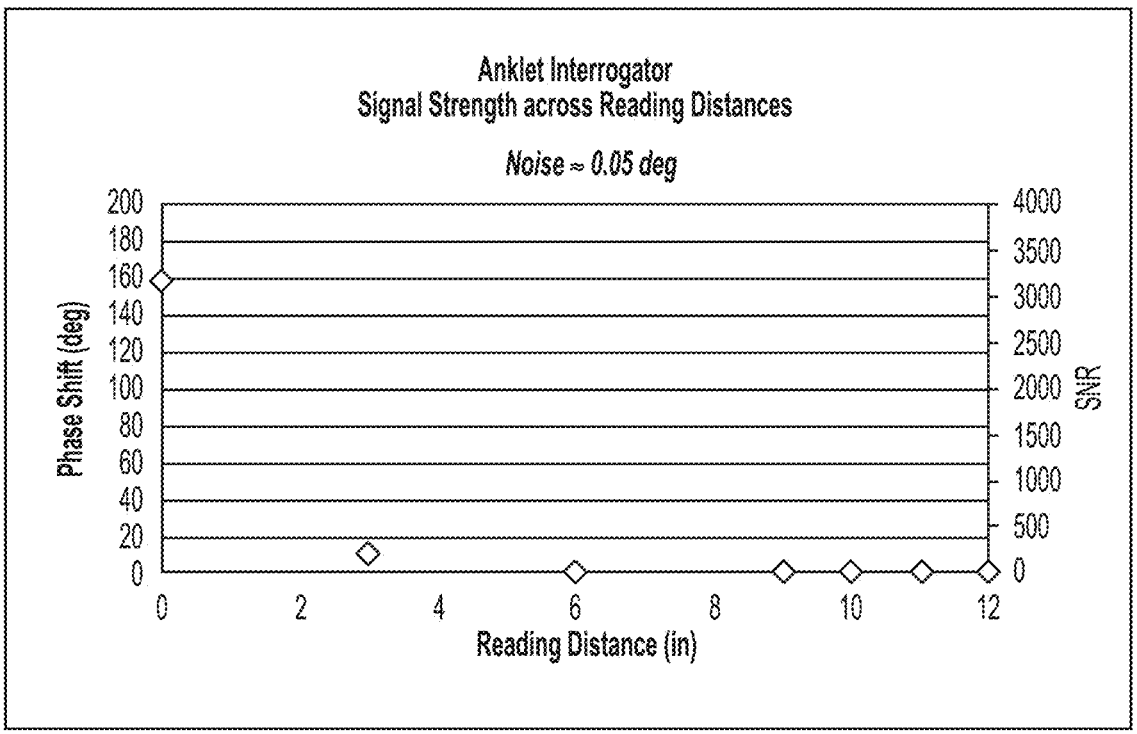
Figure 22:
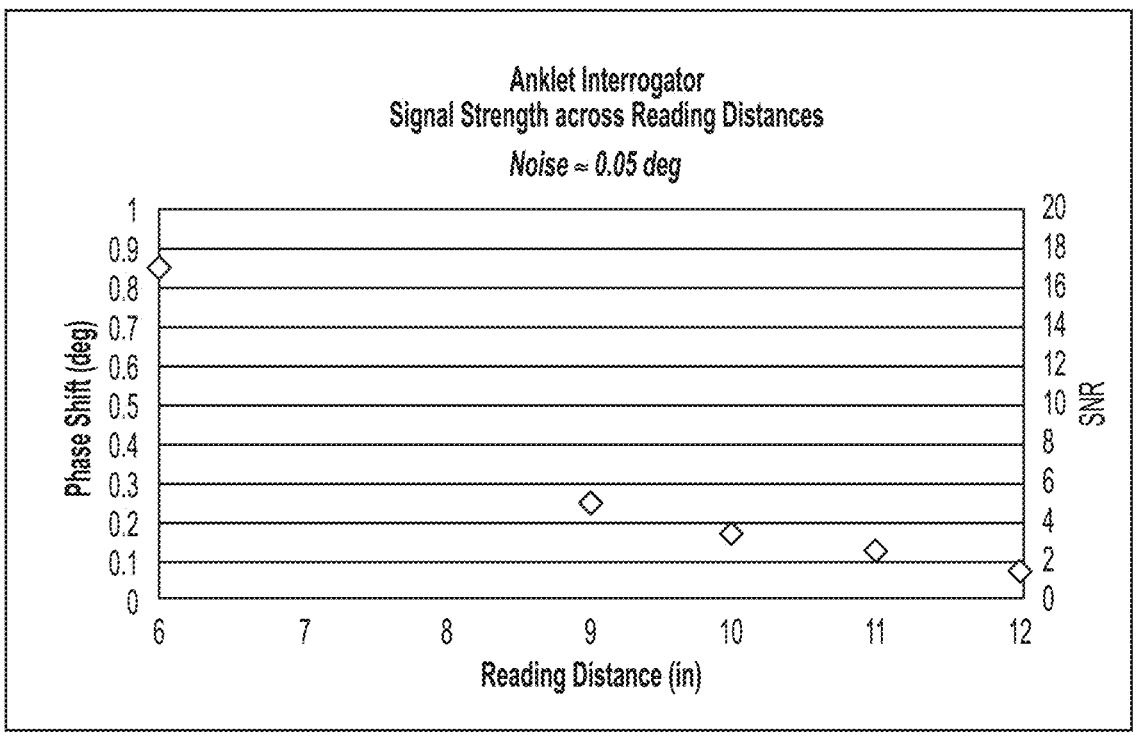
Figure 23:
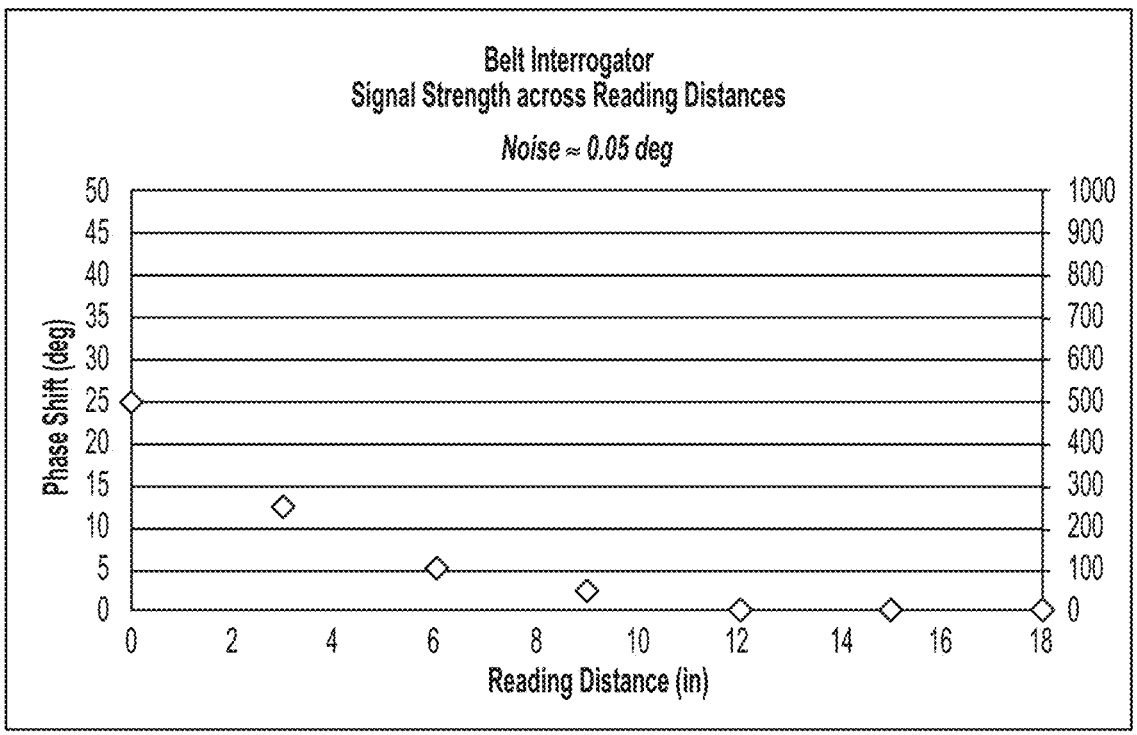
Figure 24:
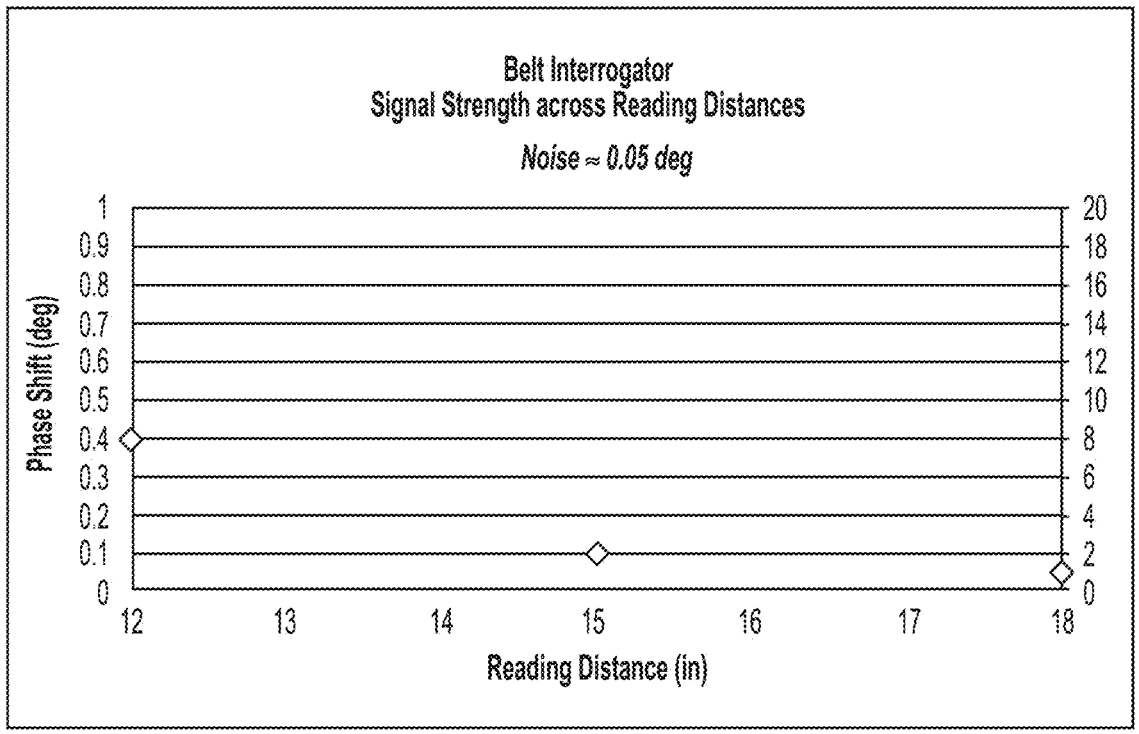
Figure 25:
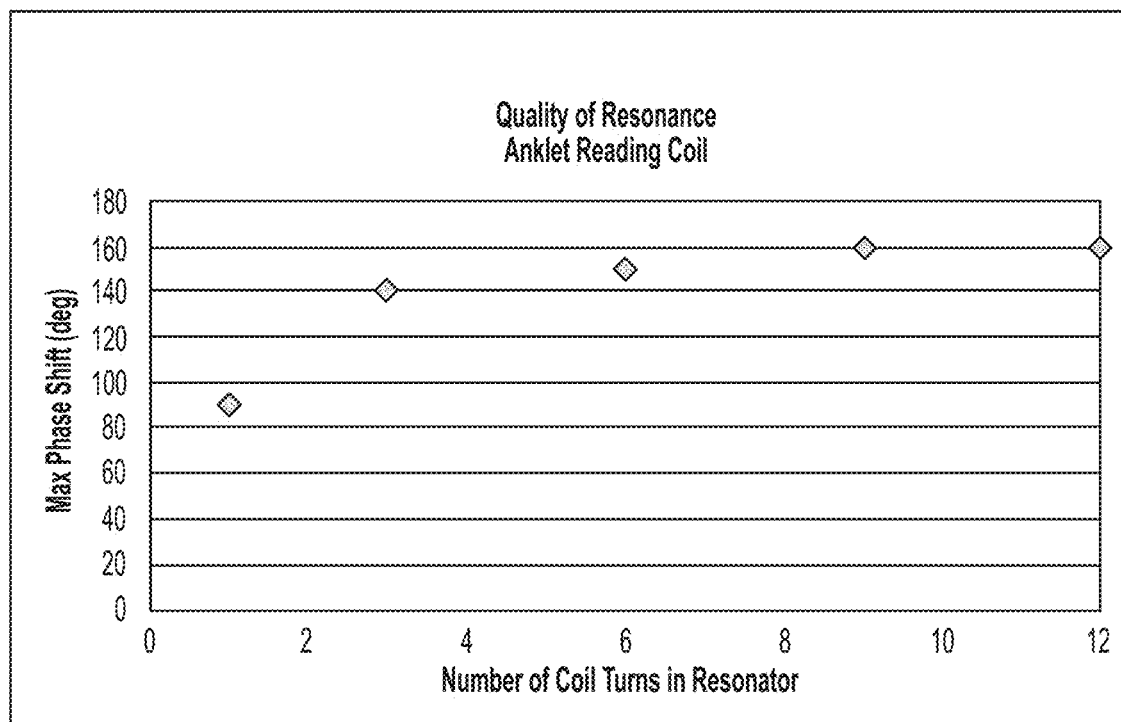

FIGS. 17-19 provide pressure data for various embodiments, while FIG. 20 provides a schematic showing different features of existing systems and an embodiment of the present disclosure using a magnetic coupling and a radio link.

FIGS. 21-25 provide data on a wireless insole reading range according to exemplary embodiments of the present disclosure. For all sensors, data was acquired with a non-optimized sensor and a non-optimized interrogation system. The impedance analyzer operated at 0.5V across the interrogating coil (instrument limit). Industry RFID interrogators frequently use >10V to increase sensitivity, and frequently have interrogation distances of >1 m for resonant tags approximately 1 cm.

It is understood that the above-described devices and methods are merely non-limiting examples of embodiments of the devices and methods disclosed herein.

Exemplary embodiments of the present disclosure include resonators that operate in the audible acoustic range. Existing systems typically stipulate stimulation in the ultrasound range.

Bandwidth of the acoustic transmitter and/or receiver in exemplary embodiments of the present disclosure is much lower than standard ultrasound crystals. In certain embodiments, a unique probe may be developed for this application in the 1-20 kHz range.

Mechanical resonators are most sensitive to gauge pressure, and only to the first several hundred mmHg, after which sensitivity drops considerably. Therefore, it is not possible simply to use or test any commercially available pressure sensor with a micromachined diaphragm, which have chambers underneath which are frequently hermetically sealed under vacuum. In the case of vacuum sealed, commercially available pressure sensors, the gauge pressure across the diaphragm at the physiological range is >800 mmHg, which offers negligible pressure sensitivity if used as a mechanical resonator.

Figure 40:
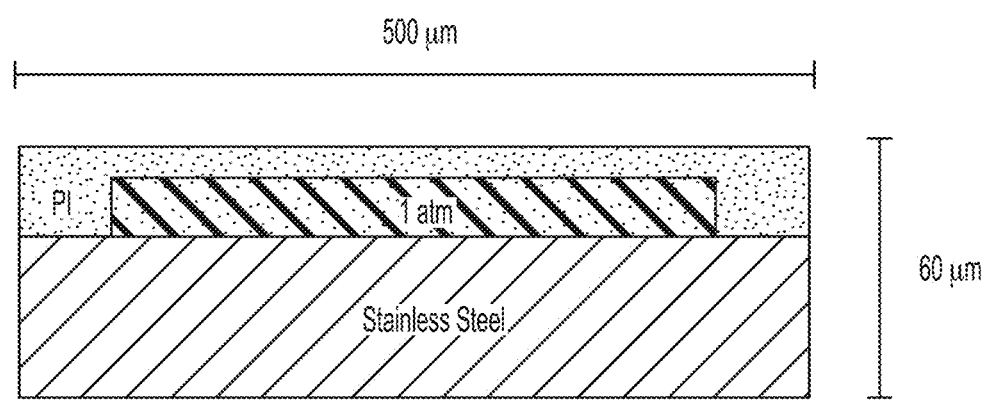
FIG. 40 illustrates a schematic of an exemplary embodiment of a resonator according to the present disclosure.

An exemplary embodiment of a prototype resonator is square polyimide diaphragm (500 um long, 5 um thick) over a closed air chamber, as shown in FIG. 40. In this embodiment, a square diaphragm made of polyimide over an air chamber is bonded to stainless steel substrate.

Modification of the standard equation for determining the resonance frequency of such a diaphragm (Roark) yields the following expression for resonance frequency with a strong pressure dependence $$F(p) = \frac{36}{2\pi}\sqrt{\frac{Dg}{a^4 \cdot (w+p)}}$$

where $$D = \frac{Et^3}{12(1-v^2)}$$

is the flexural rigidity of the diaphragm, v is the poisson ratio of the diaphragm material, E is the elastic modulus of the diaphragm material, t is the diaphragm thickness, a is the square diaphragm length, g is the gravitational constant, w is the weight of the diaphragm per unit area, and p is externally applied pressure (gauge pressure across the diaphragm).

Figure 41:
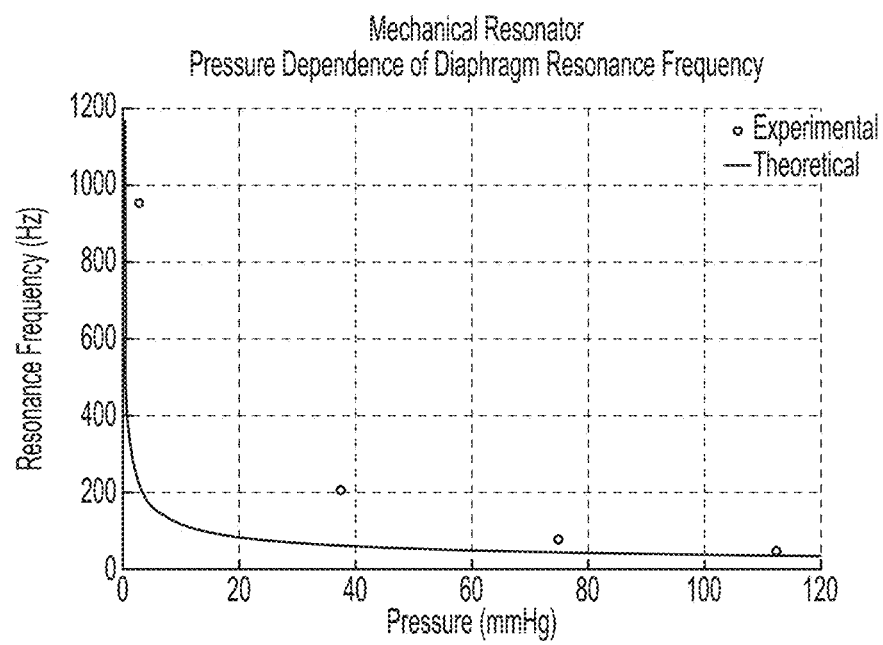
FIG. 41 illustrates resonance frequency signals at different pressures for exemplary embodiments of devices according to the present disclosure.
Figure 41:
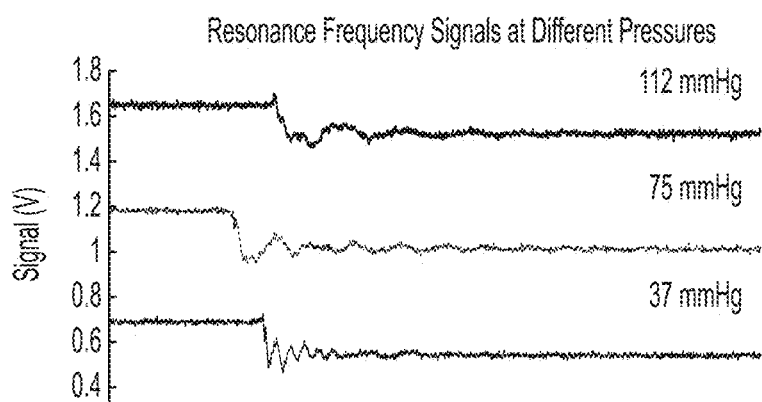
Figure 42:
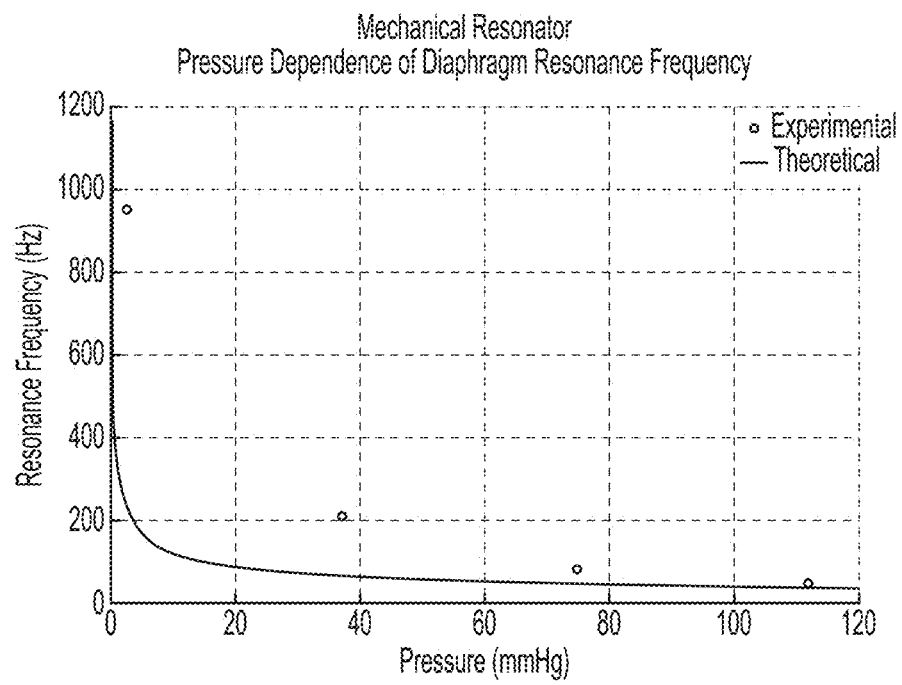
FIGS. 42-43 illustrate data showing the pressure dependence of diaphragm resonance frequency.
Figure 43:
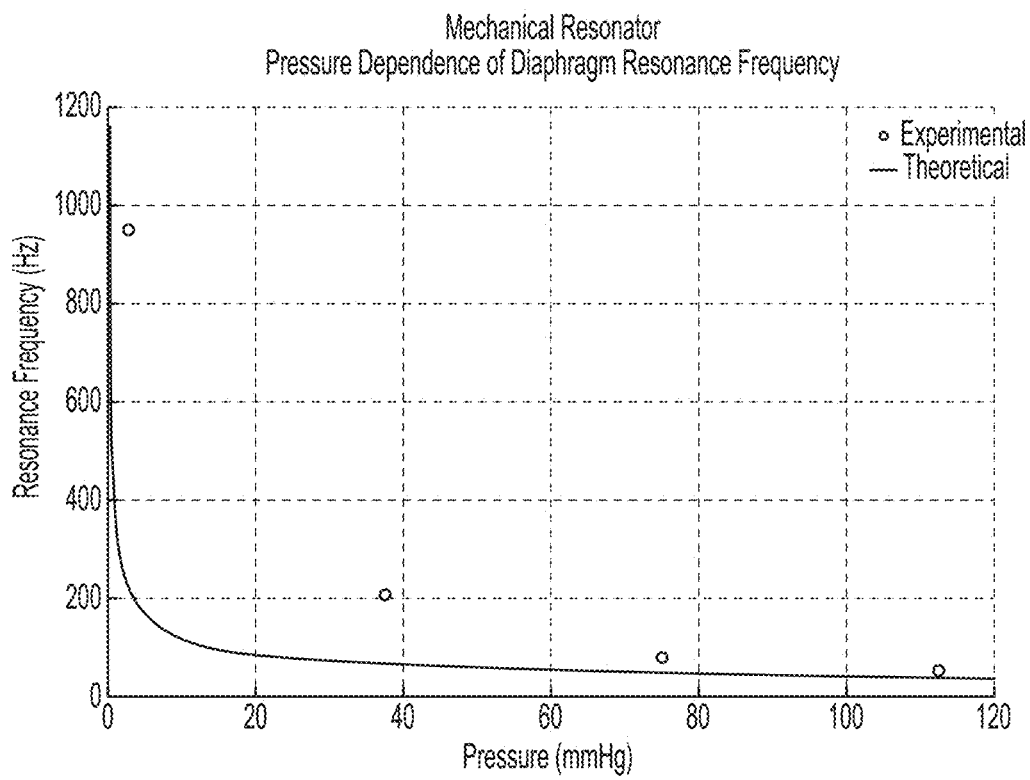

Experimental testing shows good agreement with the theory. An impulse test was applied to the prototype diaphragms at various pressures to induce resonance. FIG. 41 clearly shows the strong pressure dependence of the resonance on local pressure. FIGS. 42 and 43 show that the experimental data matches the theory well. Response of the mechanical resonator to an impulse response is shown at different pressures. Increasing pressure reduces the resonance frequency. There is a good match between experimental vs predicted resonance frequency at various pressures, for a square polyimide diaphragm 500 um long and 5um thick.

Further theoretical analysis shows that ceramic resonators should given even better pressure responses, due to their rigidity. Additionally, the outstanding mechanical stability of ceramics, particularly monocrystalline ceramics of silicon and $SiO_2$ (quartz), should lend excellent robustness and long term sensing stability.

Figure 44:
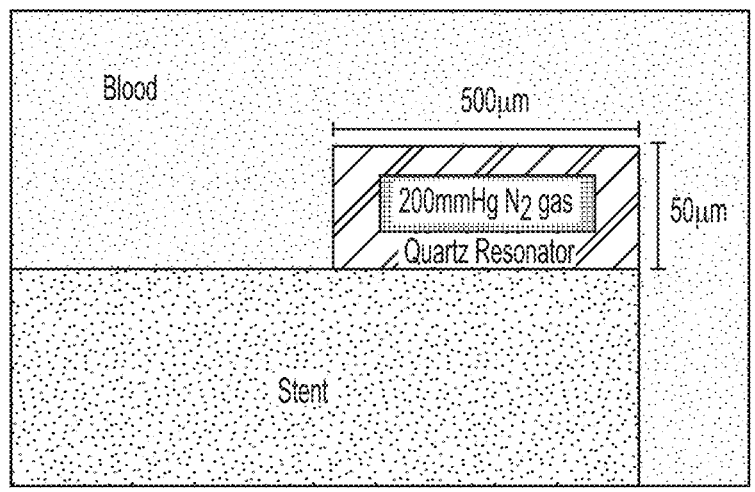
FIGS. 44-45 illustrate schematics of exemplary embodiments of resonator devices anchored to a structure according to the present disclosure.
Figure 45:
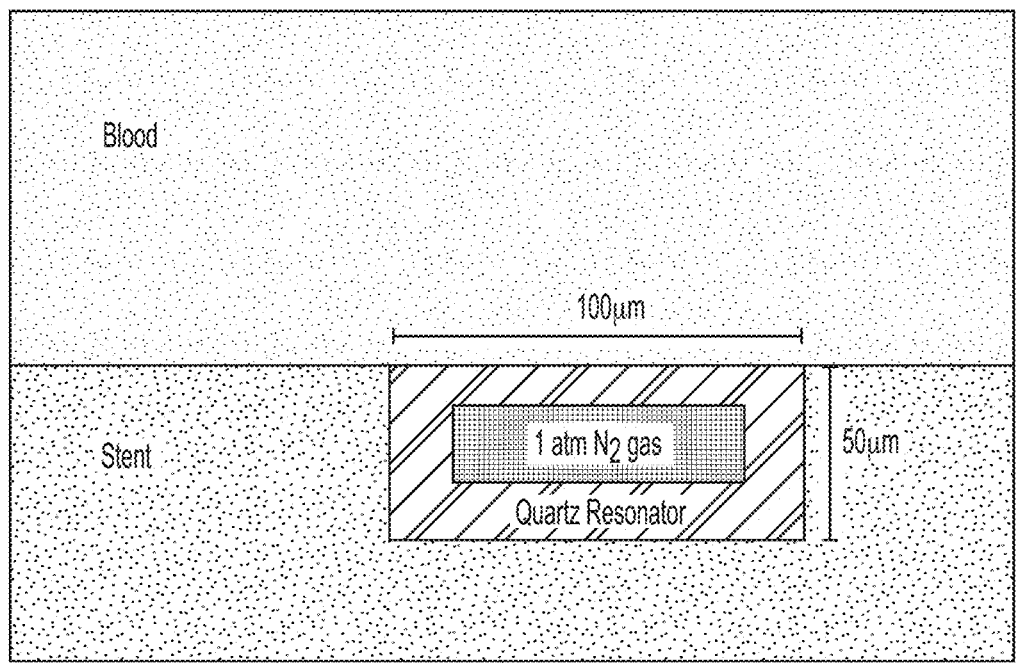

FIGS. 44 and 45 illustrate variations of a conceived ceramic resonator, anchored to a stent or stent-like structure. In FIG. 44, the resonator is bonded to the stent surface, while in FIG. 45 the resonator is embedded into the stent.

Figure 46:
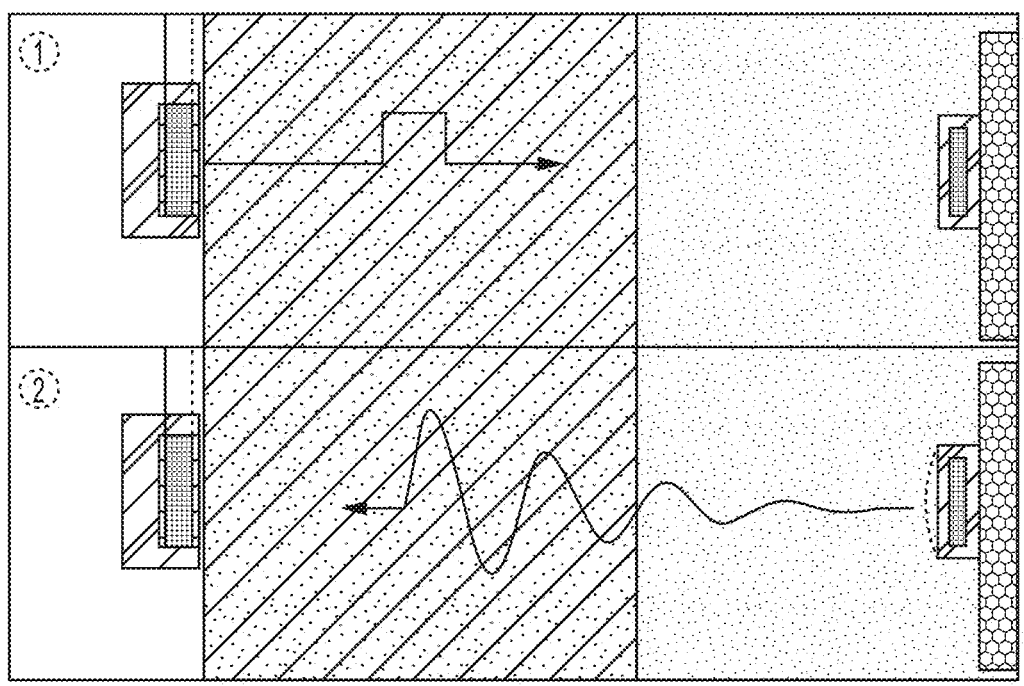
FIG. 46 illustrates a schematic of acoustic interrogation of an exemplary embodiment of a mechanical resonator according to the present disclosure.

Once percutaneously implanted, the resonator can be interrogated wirelessly by an acoustic impulse test. FIG. 46 illustrates how a piezo device at the skin surface can send a pulse to the resonator, induce vibration, and read the frequency of the vibration. In section 1 of FIG. 46, the piezo sends an impulse, either a square wave or a sine wave near the resonance frequency of the resonator. In section 2, the impulse stimulates vibration of the resonator, which produces a pressure wave with an oscillating decay at its resonance frequency. The piezo switches to listen mode, or a second receiving piezo is used, to record the resonator pressure wave.

If the resonance frequency of the resonator is sufficiently high (>1 kHz), >>100 samples of blood pressure samples can be taken during the pressure wave cycle. This should allow for a dense recreation of the blood pressure waveform.

Figure 47:
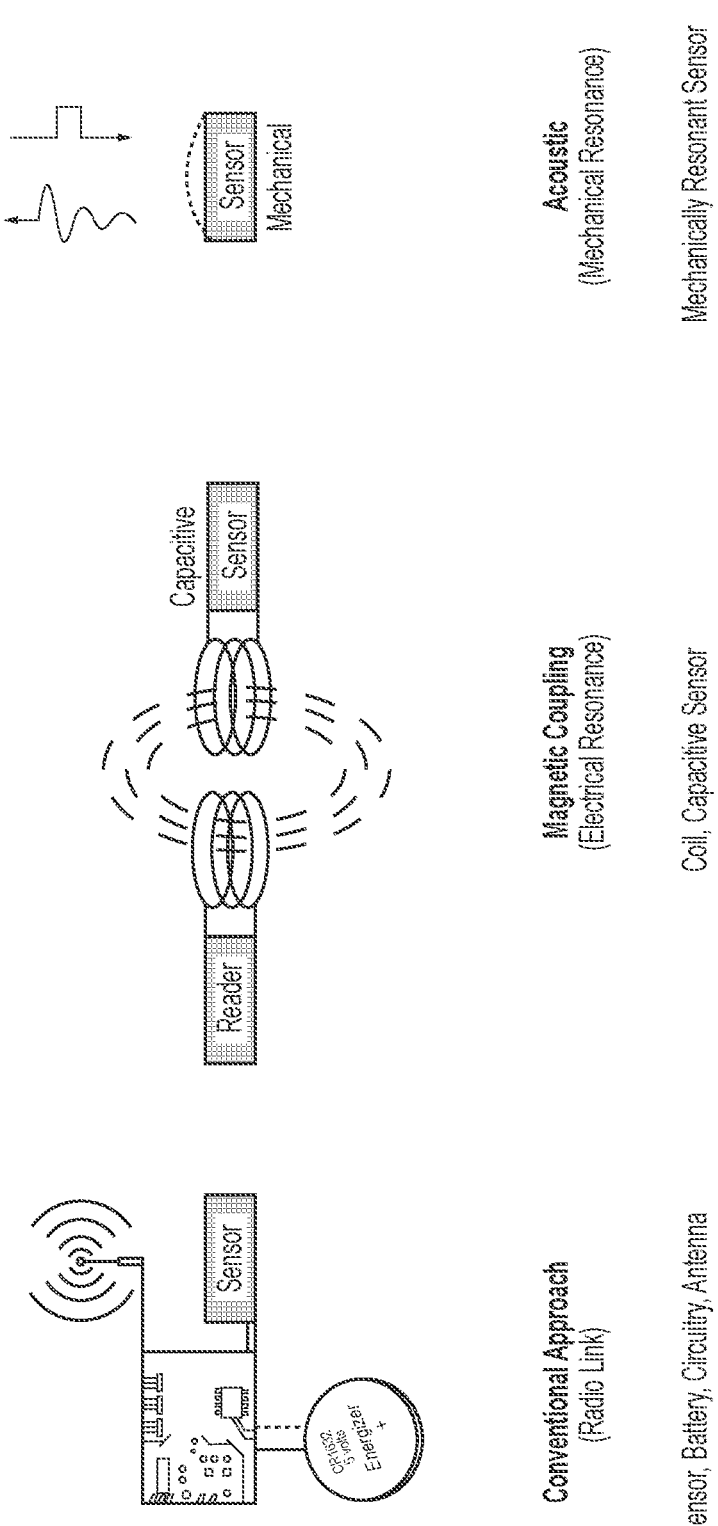
FIG. 47 illustrates schematics for wireless sensing modalities for exemplary embodiments of implantable sensors according to the present disclosure.

In the past several decades, many wireless sensing platforms have been developed which utilize a radio link to transmit the sensed data. Currently, with small Bluetooth-like radio links and smart devices, these platforms are still in full force. There is a miniaturization limit, however, due the numerous components such as power sources, circuitry, and antennas. Resonance based systems offer an alternative for wireless sensing, because resonators are typically very simple structures, can be made small, and efficiently receive and transmit energy within a certain frequency range. FIG. 47 compares these wireless sensing modalities for implantable sensors, and optical methods could also be included in this comparison. In wireless modalities for implantable sensors, conventional wireless systems are bulky, with many components. Resonant systems have fewer components, no power requirements, and can be interrogated magnetically or acoustically While well known in the physics, mechanics, and electrical literatures for over a century, resonance based sensing systems have become more intensively investigated since the 1990s, with a particular focus on electrical resonators. These electrical resonators require only a capacitive sensor and a coil to operate, and can be interrogated magnetically. Mechanical resonators, however, have not been intensively investigated for stand-alone sensing purposes.

The scientific literature is full of discussion of electrical and mechanical resonance and resonators. The engineering literature has several well recognized instances, the most prominent one being the class of resonant pressure sensors in silicon microsensors. Incidentally, these resonant pressure sensors are known to have sensitivity and stability at least an order of magnitude great than piezoresistive and capacitive sensors. In this class, a micro-beam lies on a deflecting diaphragm and is induced into resonance. Pressure deflects the diaphragm and changes the strain on the beam, whose resonance frequency then shifts. This shift is monitored by piezoresistors on the beam, which are then processed by circuitry on or near the transducer chip. An important aspect is that most declared "resonant sensors" operate similarly to this class of sensors and are not stand-alone, passive resonant sensors which can be wirelessly interrogated.

Significant intellectual property exists on the class of stand-alone, passive mechanical resonators. Included is an appendix table with examples of differences between the disclosed invention and the relevant patents. The significant point is that the inventions are largely undeveloped and, without a known exception, utilize a very different acoustic frequency range. The work in patents is done predominantly in the medical ultrasound range (MHz), whereas the disclosed invention here operates in the audible range (<20 kHz). Additionally, and related to this distinction, the method of interrogation of the patented inventions is frequently different from that of this disclosed invention.

Exemplary embodiments of the present disclosure provide numerous non-obvious advantages over existing systems. For example, the analytic solutions for resonance frequency of diaphragms and beams do not contain explicit pressure terms, and thus the pressure dependence is not obvious. Minor modifications of the formulas readily yield pressure dependence, but the insight to make them must first be had. In addition, the mechanism of sensing is fundamentally different from that of most silicon-based resonant pressure sensors. Most silicon-based resonant pressure sensors focus on inducing a pressure dependent strain on a resonating beam. This is typically done by deflecting the mechanical base on which the beam lies, or by deflecting another mechanical member onto the beam. IE, the resonance frequency of the sensing element is not directly shifted by local pressure. In our case, resonance frequency of our disclosed invention is directly shifted by local pressure.

Furthermore, the acoustic frequency range of the disclosed invention is fully audible (<20 kHz) rather than very high ultrasound (MHz). The largely undeveloped inventions covered in the scientific and patent literature typically operate in the medical ultrasound frequency range, which is 2 to 4 orders of magnitude higher than that of the disclosed invention here. The interrogation systems for this prior art are typically standard medical ultrasound probes, which limits the frequency range of the implantable sensors. Additionally, embodiments of the disclosed invention are only sensitive to low levels (several 100 mmHg) of gauge pressure across the diaphragm. That is, silicon transducers with diaphragms over vacuum sealed chambers (most of them) will not exhibit significant pressure dependence of their resonance frequency; at sensing levels, gauge pressure across the diaphragm is >800 mmHg. For example, the theory of the disclosed invention must be understood, and additionally, an off the shelf transducer cannot be used to empirically validate that theory.

To date, numerous systems exist for attempting to measure intravascular blood pressure, but all have significant limitations. For implantable devices, miniaturization and powering are the key limitations. For noninvasive devices (optical, tonometry), blood pressure waveforms can easily be generated, but scaling them with accurate systolic and diastolic values has been a persistent challenge.

Embodiments of the disclosed invention offer a solution, by providing simple passive sensor which can be anchored onto stent-like structure and be acoustically interrogated. The sensor can be made extremely small (low micron), and can be made of extremely stable ceramics (SiO2) to confer long term sensing stability. Additionally, the device has strong pressure sensitivity, enabling tenths of mmHg to be accurately measured In one example, a mechanical resonator can be configured as an implantable blood pressure sensor capable of measuring varying low, medium, and high pressure ranges and operating in one of the wireless modalities shown in FIG. 47.

Figure 48:
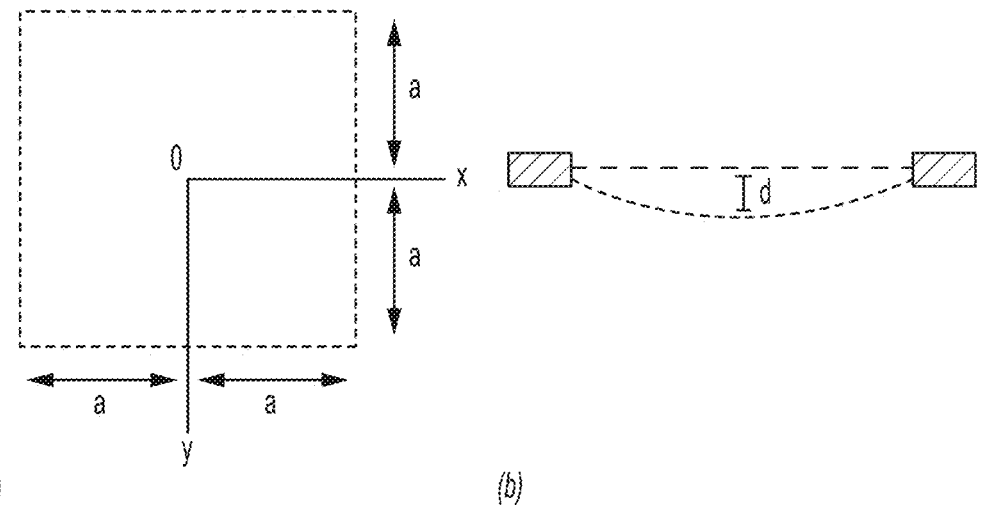
FIG. 48 illustrates a coordinate system and a schematic of an exemplary embodiment of an analytical model according to the present disclosure.

FIG. 48(*a*) illustrates a coordinate system, while FIG. 48(*b*) provides an illustration for an analytical model. In this example, 2*a*=length of square diaphragm; t=thickness; d=deflection.

Analytic Expression for Resonance Frequency

In an air environment, the analytical solution for the natural resonance frequency of a square plate with clamped edges $$f_0 = \frac{36}{2\pi} \sqrt{\left(\frac{D}{a^4}\right) \cdot \left(\frac{1}{q}\right)} \tag{11a}$$

where $$D = \frac{Et^3}{12(1-v^2)}$$

is the flexural rigidity of the diaphragm, a is the square diaphragm length and q is the load on the diaphragm including its weight per unit area and applied pressure. Here, the spring constant of the diaphragm is $$K = \sqrt{\left(\frac{324 \cdot D}{\pi^2 a^4}\right)}.$$

Figure 49:
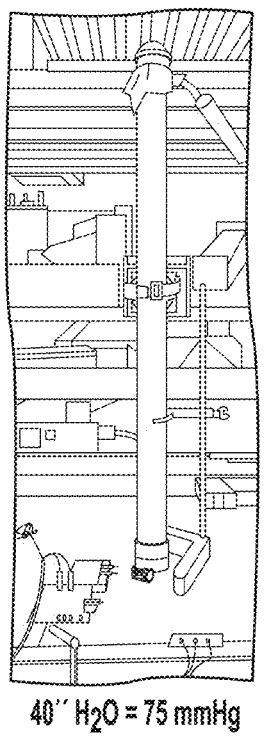
FIGS. 49-51 illustrate an experimental setup used to obtain results previously shown in FIGS. 41-43.
Figure 50:
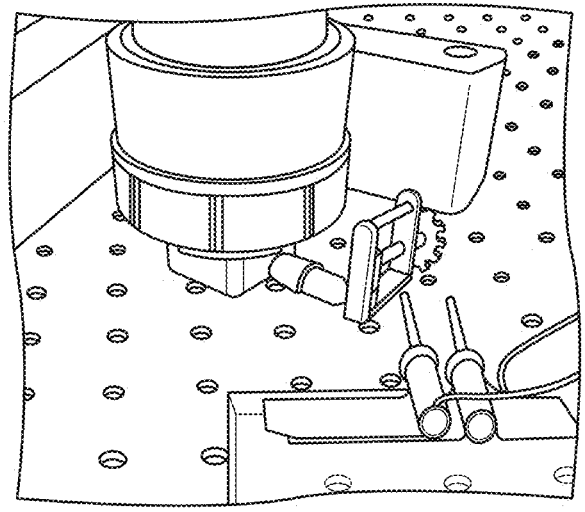
Figure 51:
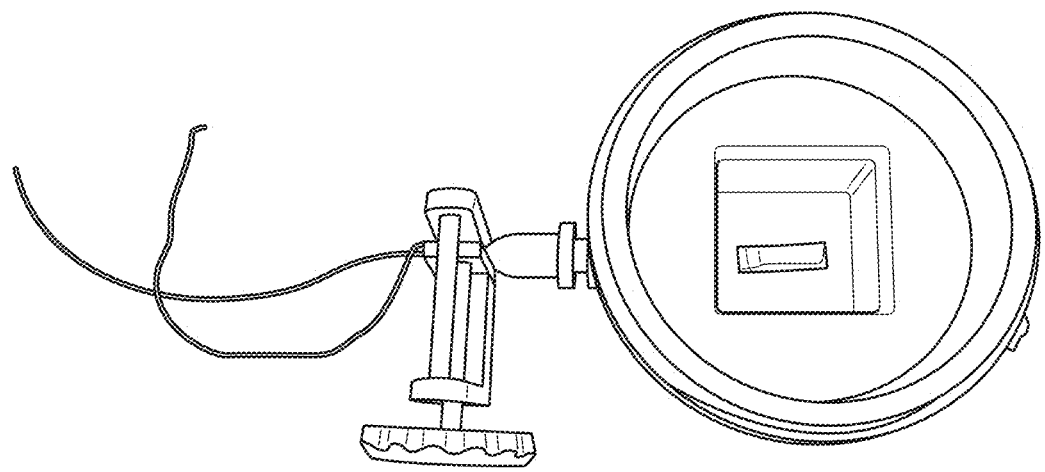
Figure 52:
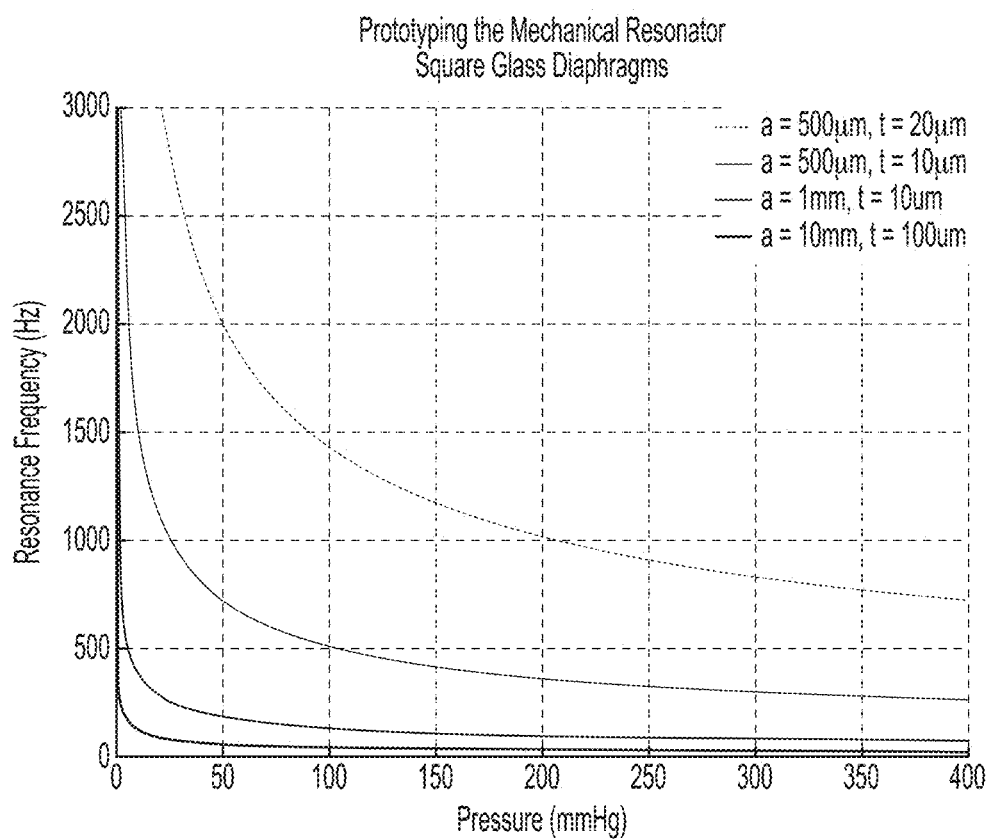
FIGS. 52-53 illustrate frequency versus pressure data in the audible range obtained from exemplary embodiments of resonators according to the present disclosure.
Figure 53:
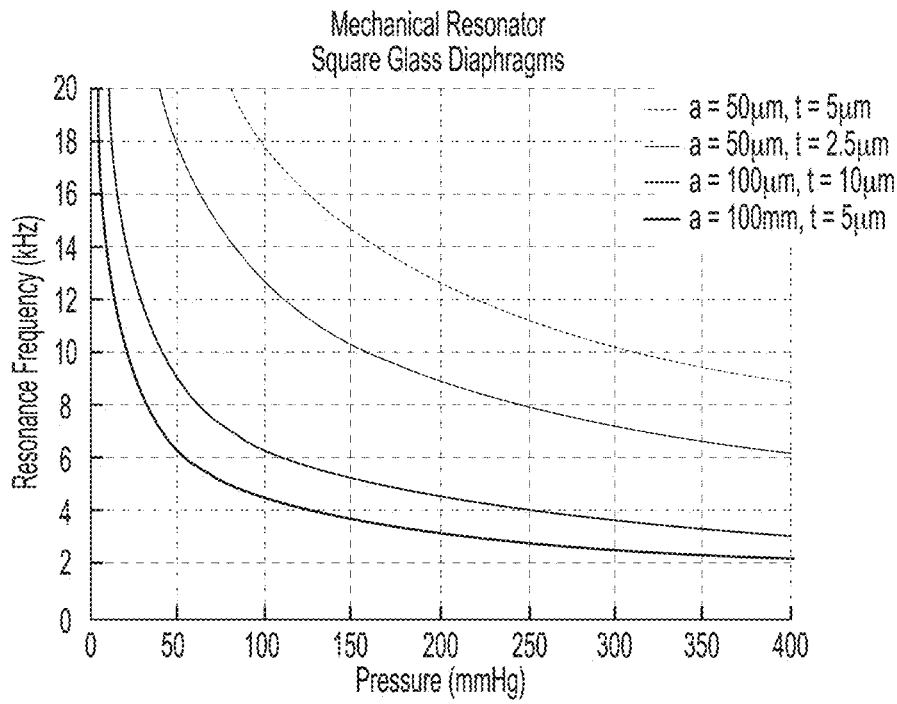

FIGS. 49-51 show an experimental setup used to obtain results previously shown in FIGS. 41-43, and FIGS. 52-53 illustrate frequency versus pressure data obtained prototyping and development in the audible range.

Figure 54:
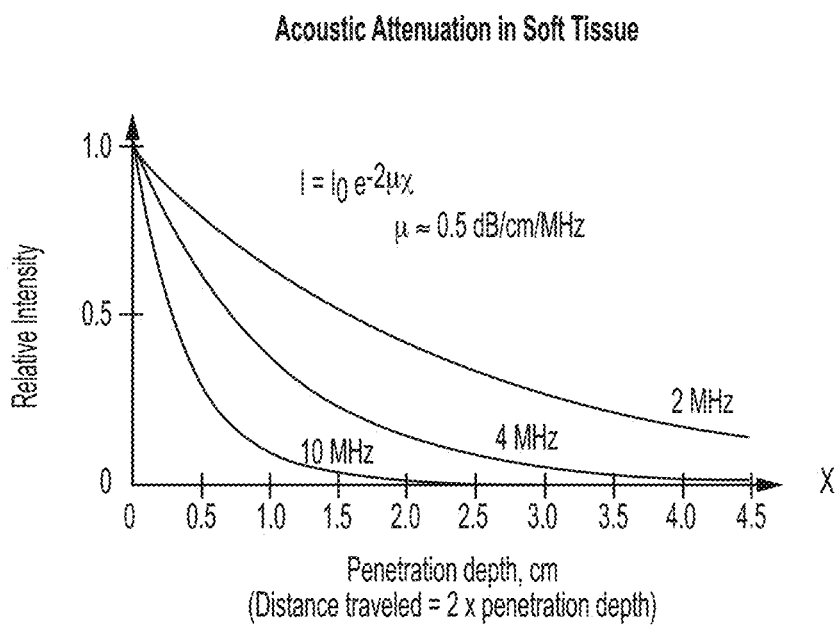
FIGS. 54-55 illustrate data showing the penetration of audible acoustic waves in soft tissue.
Figures 55, 56, 57:
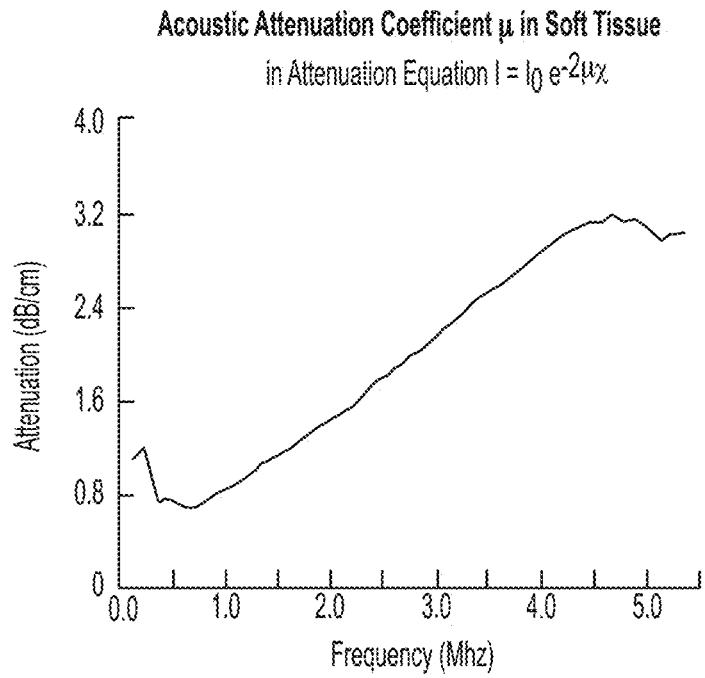
FIG. 56 illustrates the level of acoustic energy that can be delivered to a resonator for different materials according to the present disclosure.
FIG. 57 illustrates the reflected pressure ratio and reflected power ratio for soft tissue in combination for different materials.

FIGS. 54-55 illustrate the high penetration of audible acoustic waves in soft tissue. FIG. 54 demonstrates ultrasound attenuation occurs exponentially with penetration depth, and increases with increased frequency. The curves show the relative intensity of ultrasound at a particular frequency as a function of penetration depth in a medium with an attenuation coefficient of (0.5 db/cm)/MHz. The total distance traveled by the ultrasound pulse and echo is twice the penetration depth.

FIG. 55 demonstrates an attenuation function of a phantom measured using the pulse-echo substitution method. As shown, in the frequency range of 1.2 to 4.4 MHz, the least squares line is y=0.0767+0.692 x. The linear correlation coefficient is 0.9996. FIG. 56 is a chart showing the high level of acoustic energy that can be delivered to the resonator for different materials. FIG. 57 shows the reflected pressure ratio and reflected power ratio for soft tissue in combination with glass, stainless steel, and air, where:

$$\text{Reflected Pressure} = \frac{Z_2 - Z_1}{Z_2 + Z_1}$$

$$\text{Reflected Intensity}\left(\frac{\text{Power}}{\text{Area}}\right) = (\text{Reflected Pressure})^2$$

Figure 58:
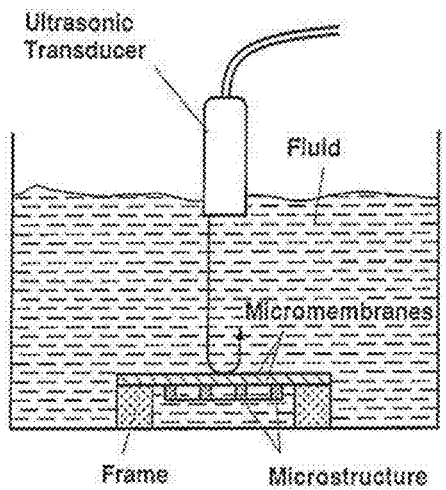
FIGS. 58-60 illustrate a schematic of an experimental set up for ultrasonic measurements and data obtained from the experiment.
Figure 59:
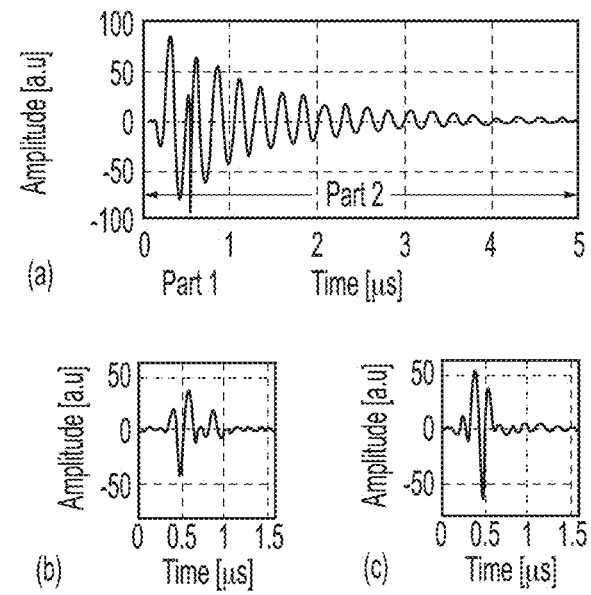
Figure 60:
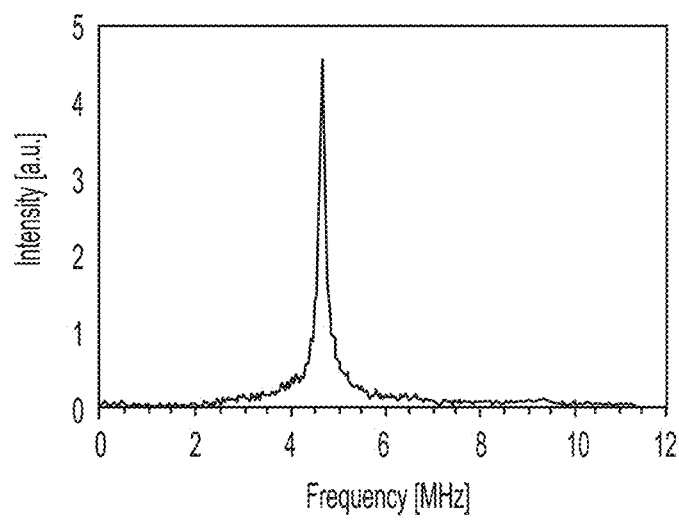

FIGS. 58-60 illustrate a schematic of an experimental set up for ultrasonic measurements and data obtained from the experiment, as disclosed in M. W. Borner et. al., Sensors and Actuators A 46-47 (1995) 62-65. FIG. 58 illustrates the schematic for the measurements, while FIG. 59 illustrates amplitude versus time data for (a) a micromembranes supported by a nickel honeycomb structure; (b) a membrane without the microstructure; and (c) the honeycomb structure alone. As shown in the figure, the echo from the micromembranes consists of two parts, with the first representing the initial signal and the second part attributed to vibrations of the membranes. As shown, echoes from the membrane or microstructure alone do not show the second part of the signal. FIG. 60 shows a Fourier transform of the signal, where the resonance frequency of the micromembranes can be seen.

As demonstrated herein, resonators used as implantable sensors provide numerous advantages, including no on-site power source or circuitry requirements, very small, and a robust design. Mechanical resonators provide numerous advantages (e.g. over electrical resonators), including the fact that non-electrical, extremely small mechanical resonator sensors can be implanted. In addition, mechanical resonators provide incredible sensitivity, given how sensitive mechanical resonance is to external pressure, and can be tailored to specific pressure ranges. Mechanical resonators theoretically excellent readout range given how well acoustic signals travel through the body. In addition, mechanical resonators have much more sensing stability over time, again because electronics are not necessary, and an elastic ceramic (quartz, glass, silicon, whatever) will not plastically deform over time. Furthermore, mechanical resonators provide for pulsewave recreation because the resonance frequency is high enough to permit dozens of samples per second in an unoptimized sensor, and possibly hundreds per second in an optimized sensor.

In addition, mechanical resonators provide audible acoustic (<10 kHz) interrogation rather than ultrasound and inexpensive piezoelectrics can be used instead of expensive ultrasound crystals and devices. Mechanical resonators provide much simpler readout electronics with inexpensive piezoelctrics and without frequency sweeps utilizing a simple, one-time acoustic pulse and then listen for the resonance echo. Furthermore, mechanical resonators can be configured with a very small size (μm range in any dimension). In certain embodiments, mechanical resonators can be sized small enough to be coupled to a stent and/or for percutaneous delivery to implantation size.

All of the apparatus, devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:

U.S. Pat. No. 3,640,271
U.S. Pat. No. 5,619,997
U.S. Pat. No. 6,312,380
U.S. Pat. No. 6,461,301
U.S. Pat. No. 6,770,032
U.S. Pat. No. 6,855,115
U.S. Pat. No. 6,959,608
U.S. Pat. No. 7,452,334
U.S. Pat. No. 7,574,792
U.S. Pat. No. 7,686,762
U.S. Pat. No. 8,162,839
U.S. Patent Publication 2004/0211260
U.S. Patent Publication 2008/0281210
U.S. Patent Publication 2013/0137958
PCT Patent Publication WO 1995020769
PCT Patent Publication WO 2010081134
PCT Patent Publication WO 2001012092
EP 0904009
An Introduction to MEMS (Micro-Electromechanical Systems); PRIME Faraday Partnership
"Stentenna: A Micromachined Antenna Stent for Wireless Monitoring of Implantable Microsensors"; Takahata, Kenichi; Department of Electrical Engineering and Computer Science, University of Michigan
"Continuous In Vivo Blood Pressure Measurements Using a Fully Implantable Wireless SAW Sensor"; Murphy, Olive H.; Biomed Microdevices (2013) 15:737-749
"Fully Wireless Implantable Cardiovascular Pressure Monitor Integrated with a Medical Stent"; Chow, Eric Y.; IEEE Transactions On Biomedical Engineering, Vol. 57, No. 6, June 2010
"A Wireless Microsensor for Monitoring Flow and Pressure in a Blood Vessel Utilizing a Dual-Inductor Antenna Stent and Two Pressure Sensors"; Takahata, Kenichi et al.; Micro Electro Mechanical Systems, 2004. 17th IEEE International Conference on. (MEMS), Pg. 216-219
"MEMS Mechanical Sensor"; Beeby, Stephan et al.
Less Invasive Long Terms Implantable Blood Pressure Sensing System for Small Animal Real Time Monitoring
"Information Technology on Five Senses"; Hirose, Michitaka; Advance Industrial Science and Technology
Tactile Array (Engel, Chen et al. 2003)
High Sensitivity (ug, ng) Force and Weight Measurements (Mannsfeld, Tee et al. 2010)
Flow Measurements (Takahata, DeHennis et al. 2004)
Acoustic/Microphone in Air and Fluid Environments (Bernstein 1994)
Microfluidic Pump (Zengerle, Kluge et al. 1995)
Microfluidic Valve (Hoff 1993)
Chemomechanical Sensing (Lin, Chang et al. 2009) (Sivaramakrishnan, Rajamani et al. 2008)
Permittivity Modulation (Yamamoto 1987)
Resonant Membrane Monitoring (Andle and Vetelino 1994) (Schroth, Sager et al. 1995)
Golay Cell (Chevrier, Baert et al. 1995)
Andle, J. C. and J. F. Vetelino (1994). "Acoustic wave biosensors." Sensors and Actuators A: Physical 44(3): 167-176
Bernstein (1994). Advanced Micromachined Condenser Hydrophone. Solid-State Sensor and Actuator Workshop. Hilton Head, S.C.

Chevrier, J.-B., et al. (1995). "An infrared pneumatic detector made by micromachining technology." Journal of Micromechanics and Microengineering 5(2): 193

Engel, J., et al. (2003). "Development of polyimide flexible tactile sensor skin." Journal of Micromechanics and Microengineering 13(3): 359

Hoff (1993). Flow Characteristics of a Pressure-Balanced Microvalve. 7th International Conference on Solid-State Sensors and Actuators. Yokohama, Japan, Proceedings of Transducers: 98-101

Kovacs, G. T. A. (1998). Micromachined Transducers: Sourcebook, WCB/MacGraw-Hill Lin, G., et al. (2009). "Free swelling and confined smart hydrogels for applications in chemomechanical sensors for physiological monitoring." Sensors and Actuators B: Chemical 136(1): 186-195

Mannsfeld, S. C. B., et al. (2010). "Highly sensitive flexible pressure sensors with microstructured rubber dielectric layers." Nat Mater 9(10): 859-864.

Schroth, A., et al. (1995). A Resonant Polyimide-based Humidity Sensor. Solid-State Sensors and Actuators, 1995 and Eurosensors IX. Transducers '95. The 8th International Conference on On Solid-State Sensors And Actuators And Eurosensors IX Sivaramakrishnan, S., et al. (2008). "Electrically stretched capacitive membranes for stiffness sensing and analyte concentration measurement." Sensors and Actuators B: Chemical 135(1): 262-267

Takahata, K., et al. (2004). A wireless microsensor for monitoring flow and pressure in a blood vessel utilizing a dual-inductor antenna stent and two pressure sensors. Micro Electro Mechanical Systems, 2004. 17th IEEE International Conference on. (MEMS)

Yamamoto (1987). An integrated temperature and humidity sensor. Proceedings of the 4th International Conference on Sensors and Actuators. Tokyo, Japan, Transducers: 658-660

Zengerle, R., et al. (1995). A bidirectional silicon micropump. Micro Electro Mechanical Systems, 1995, MEMS '95, Proceedings. IEEE Margolis D J, Malay D S, Hoffstad O J, et al. Prevalence of diabetes, diabetic foot ulcer, and lower extremity amputation among Medicare beneficiaries, 2006 to 2008: Data Points #1. 2011 Feb. 17. In: Data Points Publication Series [Internet]. Rockville (Md.): Agency for Healthcare Research and Quality (US); 2011—. Available from: http://www.ncbi.nlm.nih.gov/books/NBK63602/

Boulton A J, Armstrong D G, Albert S F, Frykberg R G, Hellman R, Kirkman M S, Lavery L A, Lemaster J W, Mills J L Sr, Mueller M J, Sheehan P, Wukich D K. Comprehensive foot examination and risk assessment: a report of the task force of the foot care interest group of the American Diabetes Association, with endorsement by the American Association of Clinical Endocrinologists. AU. American Diabetes Association, American Association of Clinical Endocrinologists. SO Diabetes Care. 2008; 31(8):1679

Driver V R, Fabbi M, Lavery L A, Gibbons G. The costs of diabetic foot: the economic case for the limb salvage team. J Am Podiatr Med Assoc. 2010 September-October; 100(5):335-41

Collins, C. C., Miniature Passive Pressure Transensor for Implanting in the Eye. Biomedical Engineering, IEEE Transactions on, 1967. BME-14(2): p. 74-83

Takahata, K., et al. Stentenna: a micromachined antenna stent for wireless monitoring of implantable microsensors. in Engineering in Medicine and Biology Society, 2003. Proceedings of the 25th Annual International Conference of the IEEE. 2003.

CDC 2011 National Diabetes Facts Sheet: http://www.cdc.gov/diabetes/pubs/estimates11.htm Cavanagh P, Simoneau G, Ulbrecht J. Ulceration, unsteadiness, and uncertainty: The biomechanical consequences of diabetes mellitus. Journal of Biomechanics. Volume 26, Supplement 1, 1993, Pages 23-29, 31-40

Bembi V, Singh S, Singh P, Aneja G K, Arya T V, Arora R. Prevalence of peripheral arterial disease in a cohort of diabetic patients. South Med J. 2006 June; 99(6):564-9.

Singh N, Armstrong D, Lipsky B. Preventing Foot Ulcers in Patients with Diabetes. JAMA. Jan. 12, 2005, Vol 293, No. 2

Driver V R, Fabbi M, Lavery L A, Gibbons G. The costs of diabetic foot: the economic case for the limb salvage team. J Am Podiatr Med Assoc. 2010 September-October; 100(5):335-41.

Everett B, Groenland M. Peripheral Sensory and Supersensory Replacement System. Patent Application, US 2012019013 A1. 3 May 2012. Sensoria Fitness. http://www.sensoriafitness.com/

M. W. Borner et. al., Sensors and Actuators A 46-47 (1995) 62-65.

The invention claimed is:

1. A device comprising:
   a substrate;
   a diaphragm coupled to the substrate, wherein the diaphragm is a thin film capacitive transducer between 10 µm and 20 µm thick; and
   a chamber structure between the diaphragm and the substrate, wherein:
     the diaphragm is coupled to the substrate via an adhesive;
     the chamber structure comprises a bonding pad around the perimeter of the chamber structure;
     the chamber structure is positioned between the diaphragm and the adhesive; and
     the substrate is approximately 50 µm thick and is electrically conductive.

2. The device of claim 1 wherein the substrate and diaphragm are configured as a wireless resonant pressure sensor sized for implantation in a human artery.

3. The device of claim 1 wherein the diaphragm is approximately 15 um thick.

4. The device of claim 1 wherein the substrate is configured as an antenna.

5. The device of claim 1 wherein the device is configured to measure pressure with a linear sensitivity of approximately four percent between 0 and 400 mm Hg.

6. The device of claim 1 wherein the substrate and the diaphragm are biocompatible.

7. The device of claim 1 wherein the device is configured as a pressure sensor.

8. The device of claim 1 wherein the device is configured as an audio wave sensor.

9. The device of claim 1 wherein the device is configured as a chemical sensor.

10. The device of claim 1 wherein the device is configured as a biological sensor.

11. The device of claim 1 wherein the device is configured as an optical sensor.

12. The device of claim 1 wherein the device is configured as a pump.

13. The device of claim 1 wherein the device is configured as a valve.

14. The device of claim 1 further comprising a first electrode coupled to the diaphragm and a second electrode coupled to the substrate.

15. A method of fabricating a thin film capacitive transducer, the method comprising;
- providing a substrate;
- providing a diaphragm, wherein the diaphragm is between 10 μm and 20 μm thick; and
- coupling the diaphragm to the substrate via an adhesive to provide a chamber structure between the diaphragm and the substrate, wherein:
    - the chamber structure comprises a bonding pad around the perimeter of the chamber structure;
    - the chamber structure is positioned between the diaphragm and the adhesive; and
    - the substrate is approximately 50 μm thick and is electrically conductive.

16. The method of claim 15 further comprising inserting the chamber structure between the diaphragm and the substrate before coupling the diaphragm to the substrate.

17. The method of claim 16 wherein the diaphragm and chamber structure are constructed using photolithography.

* * * * *